United States Patent [19]

Konno et al.

[11] Patent Number: 5,786,355
[45] Date of Patent: Jul. 28, 1998

[54] 4,6-DIARYLPYRIMIDINE DERIVATIVES AND SALTS THEREOF

[75] Inventors: Yasuo Konno; Kenji Nozaki; Shozo Yamada, all of Hanno; Tetsuji Asao, Tokorozawa; Takashi Suzuki, Hanno; Masayasu Kimura, Toyama, all of Japan

[73] Assignee: Taiho Pharmaceutical Co., Ltd., Tokyo, Japan

[21] Appl. No.: 750,197

[22] PCT Filed: Apr. 12, 1996

[86] PCT No.: PCT/JP96/01022

§ 371 Date: Nov. 27, 1996

§ 102(e) Date: Nov. 27, 1996

[87] PCT Pub. No.: WO96/32384

PCT Pub. Date: Oct. 17, 1996

[30] Foreign Application Priority Data

Apr. 13, 1995 [JP] Japan .................................. 7-088284

[51] Int. Cl.$^6$ .................. A61K 31/535; A61K 31/495; C07D 413/00; C07D 403/00
[52] U.S. Cl. .................. 514/235.8; 514/252; 514/275; 544/122; 544/295; 544/297; 544/331; 544/332
[58] Field of Search .................. 544/297, 331, 544/332, 295, 122; 514/275, 235.8, 252

[56] References Cited

PUBLICATIONS

Anjuneyulu, A.S.R. et al. "synthesis and characterization of some new oxygen and nitrogen heterocyclics: Part II 3,5–diarylisoxazoles, pyrazoles and 4,6–diarylpyrimidines" Indian Journal of Chemistry vol. 34B, Nov. 1995, pp. 933–938.

Anjaneyulu et al. (Indian J. Chem., Sect B: Org. Chem. Incl. Med. Chem. (1995), 34 B (11), 933–938.

Ankhiwala (J. Inst. Chemists (India), vol. 62, pp. 115–116, 1990.

Desai et al. (Oriental Journal of Chemistry vol. 9, No. 3 (1993) 262–263.

Mahmoud et al. (Indian J. Chem., Sect. B: Org. Chem. Incl. Med. Chem. (1996), 34 B (11), 915–919, 1995.

Ankhiwala (J. Indian Chem. Soc. (1989), 66 (6), 417–418.

*Primary Examiner*—Mukund J. Shah
*Assistant Examiner*—Bruck Kifle
*Attorney, Agent, or Firm*—Sughrue, Mion, Zinn, Macpeak & Seas, PLLC

[57] ABSTRACT

Described are a 4,6-diarylpyrimidine derivative represented by the following formula (1):

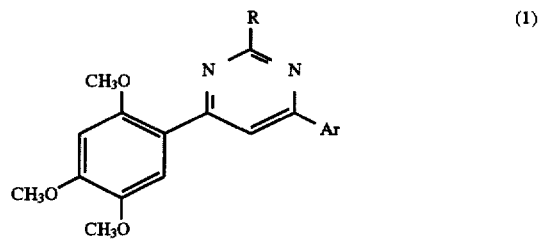

wherein R represents a heterocyclic ring which may be substituted by one to four lower alkyl groups or an amino group and Ar represents a phenyl, naphthyl or aromatic heterocyclic group which may have one to four substituents, and a salt thereof; a preparation process therefor; and a pharmaceutical containing it as an effective ingredient. It has excellent neovascular inhibitory action and is useful as a therapeutic agent for solid cancer, rheumatism, diabetic retinopathy or psoriasis.

12 Claims, No Drawings

4,6-DIARYLPYRIMIDINE DERIVATIVES AND SALTS THEREOF

TECHNICAL FIELD

The present invention relates to a novel 4,6-diarylpyrimidine derivative or salt thereof which has excellent neovascular inhibitory action and is therefore useful as a pharmaceutical typified by a therapeutic agent for solid cancer, rheumatism, diabetic retinopathy or psoriasis; its preparation process and a pharmaceutical containing it.

BACKGROUND ART

The blood vessel is a very important organ for animals. In recent years, it has been found that abnormal neovascular formation becomes an incentive to the morbid state or a factor for the worsening of the morbid state in the diseases such as malignant tumor, rheumatism, diabetic retinopathy and psoriasis. From such a viewpoint, there has been an attempt to search for a therapeutic agent for the above-described diseases using neovascular inhibitory activity as an index ["Trends in Pharmacological Sciences 15(2), 33–36 (1994)"].

The conventional neovascular inhibitor, however, has not sufficient action or has a problem in safety so that it has not come to be used as a pharmaceutical yet.

An object of the present invention is therefore to provide a compound which has excellent neovascular inhibitory activity and is useful as a pharmaceutical typified by a therapeutic agent for solid cancer, rheumatism, diabetic retinopathy or psoriasis.

DISCLOSURE OF THE INVENTION

With the forgoing in view, the present inventors have conducted an extensive investigation. As a result, it has been found that a novel 4,6-diarylpyrimidine derivative represented by the below-described formula (1) has excellent neovascular inhibitory activity and is useful as a pharmaceutical represented by a therapeutic agent for solid cancer, rheumatism, diabetic retinopathy or psoriasis, leading to the completion of the present invention.

The present invention therefore provides a 4,6-diarylpyrimidine derivative represented by the following formula (1):

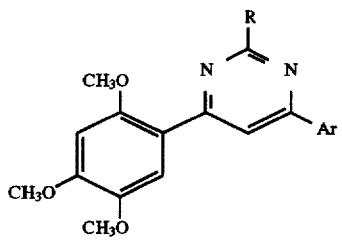

(1)

wherein R represents a nitrogen-containing heterocyclic group which may be substituted by one to four lower alkyl groups or a group —N($R^1$)$R^2$, said $R^1$ and $R^2$ being the same or different and independently representing a hydrogen atom, a lower alkyl group, a lower acyl group or a lower alkylsulfonyl group; and Ar represents a phenyl, naphthyl or aromatic, nitrogen-containing heterocyclic group which may have one to four substituents; or a salt thereof.

The present invention also provides a pharmaceutical comprising as an effective ingredient a 4,6-diarylpyrimidine derivative represented by the above formula (1) or salt thereof.

The present invention further provides a pharmaceutical composition comprising a 4,6-diarylpyrimidine derivative represented by the above formula (1) or salt thereof and a pharmacologically acceptable carrier.

The present invention further provides the use of a 4,6-diarylpyrimidine derivative represented by the above formula (1) or salt thereof as a pharmaceutical.

The present invention further provides a curative and preventive method for a disease caused by abnormal neovascular formation, which comprises administering an effective amount of a 4,6-diarylpyrimidine derivative represented by the above formula (1) or salt thereof to a mammary animal including a human being.

The present invention further provide a process for the preparation of a 4,6-diarylpyrimidine derivative represented by the above formula (1) or salt thereof.

As a 4,6-diarylpyrimidine derivative analogous to the invention compound, there is a description, for example, of 2-amino-4-(2,4-dimethoxyphenyl)-6-(3,4,5-trimethoxyphenyl)pyrimidine in "J. Heterocyclic Chem., 26, 1069–1071(1989)", which is however different from the invention compound in the substituting sites of three methoxy groups on the benzene ring at the 6-position. It makes no reference to the biological activity of the compound. In addition, in "J. INDIAN CHEM. SOC., 70, 266–267(1993)", there is a description of 2-amino-4-(2,4-dimethoxyphenyl)-6-(3,4-dimethoxyphenyl)pyrimidine, which is however different in the number of methoxy groups. In this literature, it is only described that concerning the biological activity, the compound has no antibacterial activity. In J. INDIAN CHEM. SOC., 66, 417–418(1989), described is 2-amino-4-(2-hydroxy-4-n-butoxy-5-nitrophenyl)-6-(3,4,5-trimethoxyphenyl)pyrimidine, which is however different in the substituting site of a methoxy group. Concerning the biological activity, there is only a description of antibacterial activity. Furthermore, 5-hydroxy- and 5-alkoxy-2,4,6-substituted pyrimidine derivatives are described in Japanese Patent Application No. HEI 6-47579 but they are different in the number of methoxy groups and the site of the substituent, that is, having a substituent at the 5-position. Similar to the cases of the compounds described in the above literatures, there is also no description of the neovascular inhibitory activity.

BEST MODES FOR CARRYING OUT THE INVENTION

In the above formula (1), examples of the lower alkyl group include linear or branched $C_{1-6}$ alkyl groups. Specific examples include methyl, ethyl, n-propyl, isopropyl, n-butyl, isobutyl, sec-butyl, tert-butyl, pentyl and hexyl.

In the formula (1), as the nitrogen-containing heterocyclic group represented by R, a monocylic 5- or 6-membered heterocyclic group having 1–4 nitrogen atoms and 0–1 oxygen or sulfur atom is preferred. Specific examples include pyrrolyl, oxazolyl, thiazolyl, isoxazolyl, isothiazolyl, pyrazolyl, imidazolyl, oxadiazolyl, thiadiazolyl, triazolyl, oxatriazolyl, thiatriazolyl, tetrazolyl, pyridyl, pyridazinyl, pyrimidinyl, pyrazinyl, pyrrolidinyl, pyrrolinyl, imidazoridinyl, imidazolinyl, pyrazolidinyl, pyrazolinyl, piperidyl, piperidino, piperazinyl, morpholinyl and morpholino. More preferred is a saturated, monocylic, 6-membered heterocyclic group having 1–2 nitrogen atoms and 0–1 oxygen atom, with piperidyl, piperidino, piperadinyl, morpholinyl, morpholino groups being particularly preferred.

As the nitrogen-containing heterocyclic group represented by R which has been substituted with a lower alkyl group, nitrogen-containing heterocyclic groups each of which has been substituted by 1–3 lower alkyl groups can be given. Specific examples include 2,4-dimethylpyrazolyl, 4-methylpiperazinyl, 4-ethylpiperazinyl, 4-methylpiperidyl and 4-ethylpiperidyl.

Illustrative of the lower acyl group represented by $R^1$ or $R^2$ include linear or branched $C_{1-6}$ acyl groups such as formyl, acetyl, propionyl, butyryl, isobutyryl, pivaloyl, pentanoyl and hexanoyl.

Exemplary lower alkylsulfonyl groups include linear or branched $C_{1-6}$ alkylsulfonyl groups such as methylsulfonyl, ethylsuflonyl, propylsulfonyl, n-butylsulfonyl, isobutylsulfonyl, sec-butylsulfonyl, tert-butylsulfonyl, pentylsulfonyl and hexylsulfonyl.

In the formula (1), as the aromatic nitrogen-containing heterocyclic group, among the groups represented by Ar, an aromatic, monocylic, 5- or 6-membered, heterocyclic group having 1–4 nitrogen atoms and 0–1 oxygen or sulfur atom is preferred. Specific examples include pyrrolyl, oxazolyl, thiazolyl, isoxazolyl, isothiazolyl, pyrazolyl, imidazolyl, oxadiazolyl, thiadiazolyl, triazolyl, oxatriazolyl, thiatriazolyl, tetrazolyl, pyridyl, pyridadinyl, pyrimidinyl and pyrazinyl. More preferred is an aromatic, monocyclic, 5- or 6-membered, heterocyclic group having one nitrogen atom and 0–1 sulfur atom, with pyridyl and thiazolyl groups being particularly preferred.

Examples of the substituent which the phenyl group, naphthyl group or aromatic nitrogen-containing heterocyclic group represented by Ar may have include a hydroxyl group, lower alkylsulfoamide group, lower alkylthio group, lower alkoxycarbonyl group, amino group which may be substituted by 1–2 lower alkyl groups, halogen atom, nitro group, phosphoric acid residue, nitrogen-containing heterocyclic group which may be substituted by 1–3 lower alkyl groups and lower alkoxyl group which may contain a substituent. Examples of the substituent of the lower alkoxyl group include a hydroxyl group, polyether group, amino group which may be substituted by 1–2 lower alkyl groups, amineoxide group which may be substituted by 1–2 lower alkyl groups and a monocyclic or fused-ring nitrogen-containing heterocyclic group which may be substituted by 1–3 lower alkyl groups.

Each of these substituents can be positioned at any site on each ring and 1–4 substituents which are the same or different are possible. One to three substituents, however are preferred.

Of these substituents, examples of the lower alkylsulfoamide group include linear or branched $C_{1-6}$ alkylsulfoamide groups such as methylsulfoamide, ethylsulfoamide, propylsulfoamide, n-butylsulfoamide, isobutylsulfoamide, sec-butylsufoamide, tert-butylsulfoamide, pentylsulfoamide and hexylsulfoamide groups.

Illustrative of the lower alkylthio group include linear or branched $C_{1-6}$ alkylthio group such as methylthio, ethylthio, n-propylthio, isopropylthio, n-butylthio, isobutylthio, sec-butylthio, tert-butylthio, pentylthio and hexylthio groups.

Exemplary lower alkoxycarbonyl group include linear or branched alkoxycarbonyl groups having 2–7 carbon atoms such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl and hexyloxycarbonyl groups.

Examples of the amino group which may be substituted by 1–2 lower alkyl groups include amino groups which may be mono- or di-substituted by a linear or branched $C_{1-6}$ alkyl group, such as amino, methylamino, dimethylamino, ethylamino, diethylamino, propylamino, butylamino, pentylamino and hexylamino groups.

Examples of the halogen atom include fluorine, chlorine, bromine and iodine atoms.

As the examples of the nitrogen-containing hetero-cyclic group and the nitrogen containing heterocyclic group which may be substituted by 1–3 lower alkyl groups, each of which is a substituent for the group represented by Ar, groups similar to those exemplified as R can be given.

Examples of the lower alkoxyl group include linear or branched $C_{1-6}$ alkoxyl groups such as methoxy, ethoxy, n-propoxy, isopropoxy, n-butoxy, isobutoxy, sec-butoxy, tert-butoxy, pentyloxy and hexyloxy groups.

Examples of the polyether group which is one of the substituents for the lower alkoxyl group include linear or branched $C_{1-6}$ polyether groups such as methoxymethoxy, methoxyethoxy, ethoxyethoxy and ethoxymethoxy groups.

As the examples of the amino group which may be substituted by 1–2 lower alkyl groups, amino groups exemplified above can be given.

Examples of the amineoxide group which may be substituted by 1–2 lower alkyl groups include methylaminooxide, dimethylaminooxide, ethylaminooxide, diethylaminooxide, butylaminooxide and dibutylaminooxide groups.

As the monocyclic or fused-ring nitrogen-containing heterocyclic group, a monocyclic 5- or 6-membered heterocyclic group having 1–4 nitrogen atoms and 0–1 oxygen or sulfur atom or a fused-ring heterocyclic group with which a benzene ring has been condensed is preferred. Specific examples include pyrrolyl, oxazolyl, thiazolyl, isoxazolyl, isothiazolyl, pyrazolyl, imidazolyl, oxadiazolyl, thiadiazolyl, triazolyl, oxatriazolyl, thiatriazolyl, tetrazolyl, pyridyl, pyridazinyl, pyrimidinyl, pyrazinyl, pyrrolidinyl, pyrrolinyl, imidazolidinyl, imidazolinyl, pyrazolidinyl, pyrazolinyl, piperidyl, piperidino, piperazinyl, morpholinyl, morpholino, benzothiazolyl, benzoimidazolyl and phthaliminoyl groups. Preferred are monocyclic 5- or 6-membered heterocyclic group having 1–2 nitrogen atoms and at most one oxygen atom and phthaliminoyl group, with piperidyl, piperidino, piperazinyl, morpholino, morpholinyl, imidazolyl and phthaliminoyl groups being particularly preferred.

Examples of the monocylic or fused-ring nitrogen-containing heterocyclic group which has been substituted by 1–3 lower alkyl groups include 2,4-dimethylpyrazolyl, 4-methylpiperadinyl, 4-ethylpiperadinyl, 4-methylpiperidyl and 4-ethylpiperidyl groups.

As the group represented by R in the formula (1), an amino group which may be substituted by 1–2 lower alkyl groups is preferred, with amino, dimethylamino and diethylamino groups being more preferred.

As the group represented by Ar, aromatic, monocylic, 5- or 6-membered, heterocyclic group containing 1–4 phenyl groups, naphthyl groups or nitrogen atoms each of which may contain a substituent and 0–1 sulfur atom is preferred, with phenyl, naphthyl, pyridyl and thiazolyl groups which may contain a substituent being more preferred. Particularly preferred are phenyl groups each of which has 1–3 substituents selected from the following groups (1) to (4):

(1) a lower alkylsulfoamide group, (2) an amino group which may be substituted by 1–2 lower alkyl groups, (3) a nitrogen-containing heterocyclic group, and (4) a lower alkoxyl group which may be substituted by the following (a) or (b):

(a) an amino group which may be substituted by 1–2 lower alkyl groups, (b) a monocyclic or fused-ring nitrogen-containing heterocyclic group which may be substituted by 1–3 lower alkyl groups. Of these, phenyl groups each having 1–3 lower alkoxyl groups or lower alkoxyl groups each substituted by an amino group which may be substituted by 1–2 lower alkyl groups are preferred.

Among the compounds (1) according to the present invention, preferred is a compound represented by the formula (1) wherein a group represented by Ar is a phenyl group having 1–3 substituents selected from the following groups (1) to (4):

(1) a lower alkylsulfoamide group, (2) an amino group which may be substituted by 1–2 lower alkyl groups, (3) a nitrogen-containing heterocyclic group, and (4) a lower alkoxyl group which may be substituted by the following (a) or (b):

(a) an amino group which may be substituted by 1–2 lower alkyl groups, (b) a monocyclic or fused-ring nitrogen-containing heterocyclic group which may be substituted by 1–3 lower alkyl groups and a group represented by R is an amino group which may be substituted by 1–2 lower alkyl groups. More preferred is a 4,6-diarylpyrimidine derivative represented by the formula (1) wherein Ar represents a phenyl group having has as a substituent 1–3 lower alkoxyl groups or lower alkoxyl groups each substituted by an amino group which may be substituted by 1–2 lower alkyl groups, and R represents an amino, dimethylamino or diethylamino group.

No particular limitation is imposed on the salt of the invention compound insofar as it is a pharmacologically acceptable salt. Examples include the salts with an inorganic acid such as hydrochloric acid, sulfuric acid, phosphoric acid or hydrobromic acid; and with an organic acid such as formic acid, acetic acid, propionic acid, trifluoroacetic acid, oxalic acid, malonic acid, succinic acid, maleic acid, fumaric acid, malic acid, tartaric acid, citric acid, benzoic acid, methanesulfonic acid or p-toluenesulfonic acid. The invention compound (1) or salt thereof is sometimes isolated in the form of various solvates typified by hydrates. These solvates are also embraced by the present invention.

The compound represented by the formula (1) according to the present invention can be prepared, for example, in accordance with the processes shown below by the reaction schemes 1–9.

Reaction scheme 1

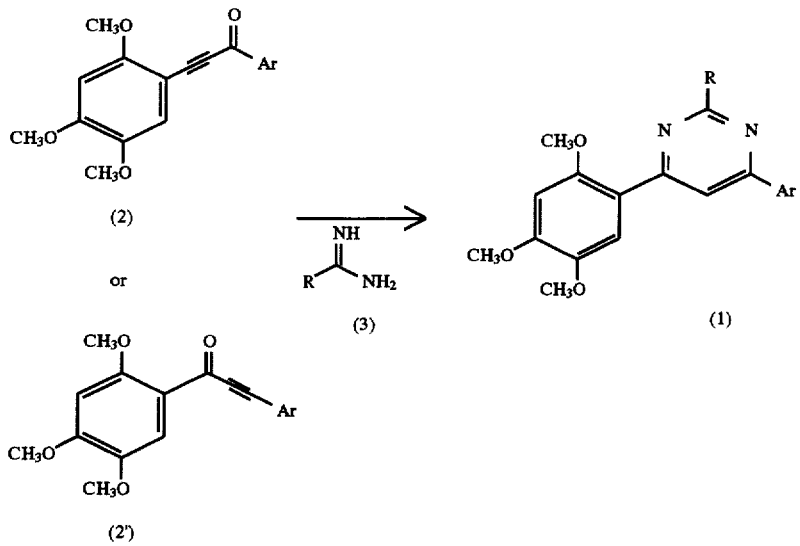

wherein Ar and R have the same meanings as defined above.

The target compound (1) of the present invention can be obtained by reacting a compound represented by the formula (2) or formula (2') with a compound represented by the formula (3) in a suitable solvent.

No particular limitation is imposed on the solvent insofar as it takes no part in the reaction. Examples include alcohols such as methanol and ethanol, ethers such as ethyl ether and tetrahydrofuran, halogenated hydrocarbons such as methylene chloride and chloroform, aromatic hydrocarbons such as benzene and toluene, aprotic polar solvents such as N,N-dimethylformamide, dimethylsulfoxide and acetonitrile, and water. They may be used either singly or in combination.

In this reaction, the compound represented by the formula (3) may be used in an amount of about 1–10 equivalents, preferably about 1–1.5 equivalents relative to the compound represented by the formula (2) or (2'). The reaction may be conducted at a temperature ranging from about room temperature to the boiling point of the solvent, preferably about 80°–170° C. The reaction time may be about 0.1–48 hours, by which the reaction proceeds advantageously.

Incidentally, when the compound represented by the formula (3) is a salt with an acidic compound, a base may be used for neutralization, or the compound represented by the formula (3) is neutralized with a base in advance to form a free state, followed by the addition to the reaction system. Illustrative of the base usable here include hydroxides of an alkali metal such as sodium hydroxide and potassium hydroxide, organic amines such as pyridine, triethylamine and piperidine, alkoxides of an alkali metal such as sodium methoxide, sodium ethoxide, potassium tertbutoxide and sodium isopropoxide, sodium acetate, potassium carbonate and sodium carbonate.

Reaction scheme 2

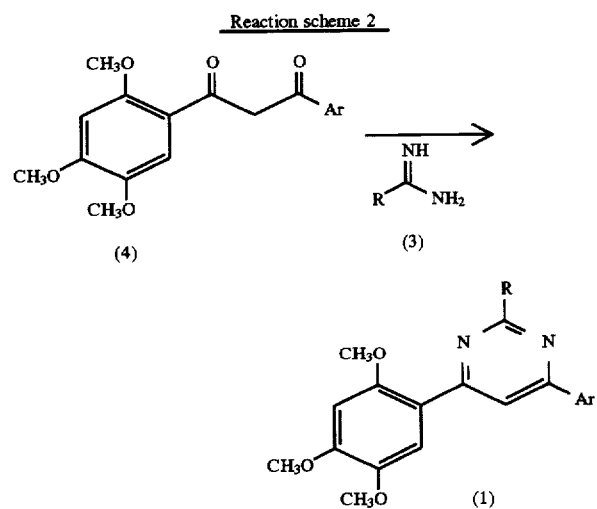

wherein Ar and R have the same meanings as defined above.

The target compound (1) of the present invention can be obtained by reacting a compound represented by the formula (4) with the compound represented by the formula (3) in a similar manner to the above Reaction scheme 1.

No particular limitation is imposed on the solvent insofar as it takes no part in the reaction. Examples include alcohols-such as ethanol, 2-butanol and tert-amyl alcohol, ethers such as ethyl ether and tetrahydrofuran, halogenated hydrocarbons such as methylene chloride and chloroform, aromatic hydrocarbons such as benzene and toluene, aprotic polar solvents such as N,N-dimethylformamide, dimethylsulfoxide and acetonitrile, and water. They may be used either singly or in combination.

In this reaction, the compound represented by the formula (3) may be used in an amount of about 1-10 equivalents, preferably about 1-1.5 equivalents relative to the compound represented by the formula (4). The reaction may be conducted at a temperature ranging from about room temperature to the boiling point of the solvent, preferably about 80°-170° C. The reaction time may be for about 0.1 hour to 48 hours, by which the reaction proceeds advantageously.

Incidentally, when the compound represented by the formula (3) is a salt with an acidic compound, as in Reaction scheme 1, a base may be used for neutralization, or the compound represented by the formula (3) is neutralized with a base in advance to form a free state, followed by the addition to the reaction system.

Reaction Scheme 3

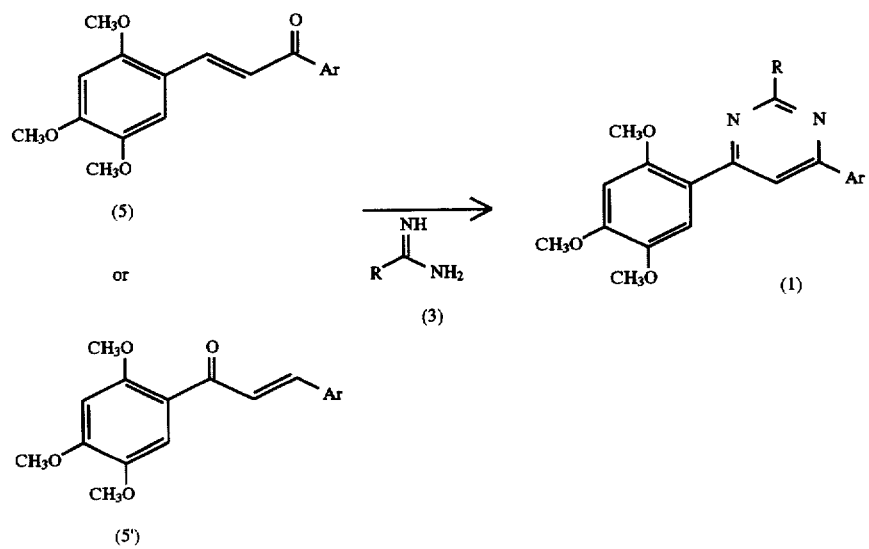

wherein Ar and R have the same meanings as defined above.

The target compound (1) of the present invention can be obtained by reacting a compound represented by the formula (5) or (5') with the compound represented by the formula (3) in a similar manner to the above-described Reaction scheme 1.

No particular limitation is imposed on the solvent insofar as it takes no part in the reaction. Examples include alcohols such as methanol and ethanol, ethers such as ethyl ether and tetrahydrofuran, halogenated hydrocarbons such as methylene chloride and chloroform, aromatic hydrocarbons such as benzene and toluene, aprotic polar solvents such as N,N-dimethylformamide, dimethylsulfoxide and acetonitrile, and water. They may be used either singly or in combination.

In this reaction, the compound represented by the formula (3) may be used in an amount of about 1–10 equivalents, preferably about 1–1.5 equivalents relative to the compound represented by the formula (5) or (5'). The reaction may be conducted at a temperature ranging from about room temperature to the boiling point of the solvent, preferably about 80°–170° C. The reaction time may be about 0.1 hour to 48 hours.

Incidentally, when the compound represented by the formula (3) is a salt with an acidic compound, in a similar manner to the above-described Reaction scheme 1, a base may be used for neutralization, or the compound represented by the formula (3) may be neutralized with a base in advance to form a free state, followed by the addition to the reaction system.

In the compounds of the formula (1) obtained according to the above Reaction schemes 1–3, when Ar contains as a substituent a lower alkoxyl group which may be substituted by a polyether group, the polyether group can be converted into a hydroxyl group as needed by reacting with hydrobromic acid, hydroiodic acid, hydrochloric acid, sulfuric acid or the like, for example, in a solventless manner or in a suitable solvent. Examples of the solvent include alcohols such as methanol and ethanol, acetic acid and water. They may be used either singly or in combination.

In the above reaction, it is preferred to use hydrobromic acid, hydroiodic acid, hydrochloric acid, sulfuric acid or the like in an amount of about 1–1000 equivalents relative to the compound containing as a substituent a lower alkoxyl group which may be substituted by a polyether group. The reaction temperature may be 0°–150° C. and the reaction time may be 1–100 hours, by which the reaction proceeds advantageously.

Among the compounds obtained according to the reaction schemes 1–3, the compound (1a) which contains an amino group as R is reacted according to the below-described Reaction scheme 4 or 5, whereby the target compound of the present invention (1b) or (1c) can be obtained.

Reaction scheme 4

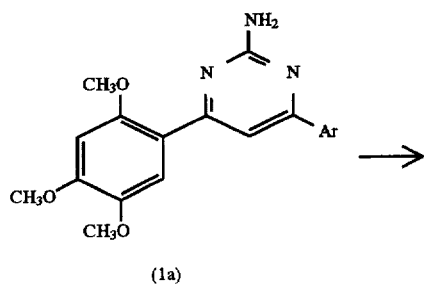

(1a)

—continued
Reaction scheme 4

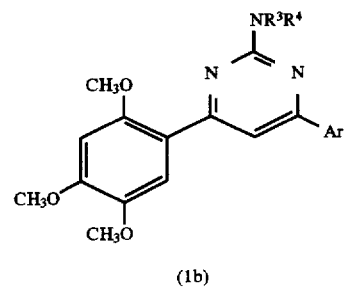

(1b)

wherein Ar has the same meaning as defined above, $R^3$ and $R^4$ are the same or different and independently represents a hydrogen atom, lower acyl group or lower alkylsulfonyl group, with the proviso that $R^3$ and $R^4$ are not hydrogen atoms at the same time.

The target compound (1b) of the present invention can be obtained by reacting the compound represented by the formula (1a) with an acid chloride or acid anhydride in a solvent or solventless manner.

Examples of the acid chloride usable here include acyl chlorides of the above-exemplified lower acyl group such as acetyl chloride, propionyl chloride, butyryl chloride, isobutyryl chloride and pivaloyl chloride; and lower alkyl sulfonic acid chlorides such as methanesulfonic acid chloride, ethanesulfonic acid chloride, propanesulfonic acid chloride and butanesulfonic acid chloride.

No particular limitation is imposed on the acid anhydride insofar as it releases the above-exemplified lower acyl or lower alkylsulfonyl group as a substituent. Examples include acetic anhydride, propionic anhydride, butyric anhydride, isobutyric anhydride, pivalic anhydride, methanesulfonic anhydride, ethanesulfonic anhydride, propanesulfonic anhydride and butanesulfonic anhydride.

No particular limitation is imposed on the solvent insofar as it takes no part in the reaction. Illustrative of the solvent include alcohols such as methanol and ethanol, ethers such as ethyl ether and tetrahydrofuran, halogenated hydrocarbons such as methylene chloride and chloroform, aromatic hydrocarbons such as benzene and toluene and aprotic polar solvents such as N,N-dimethylformamide, dimethylsulfoxide and acetonitrile. They may be used either singly or in combination.

In the above reaction, it is preferred to use the acid chloride or acid anhydride in an amount of 1–1000 equivalents relative to the compound represented by the formula (1a). The reaction may be conducted at a temperature ranging from under ice cooling to the boiling point of the acid anhydride or so. The reaction time may be about 0.1 hour to 96 hours, by which the reaction proceeds advantageously.

It is also possible to add an organic amine such as triethylamine or dimethylaniline in an amount of 1–10 equivalents to accelerate the reaction.

Reaction scheme 5

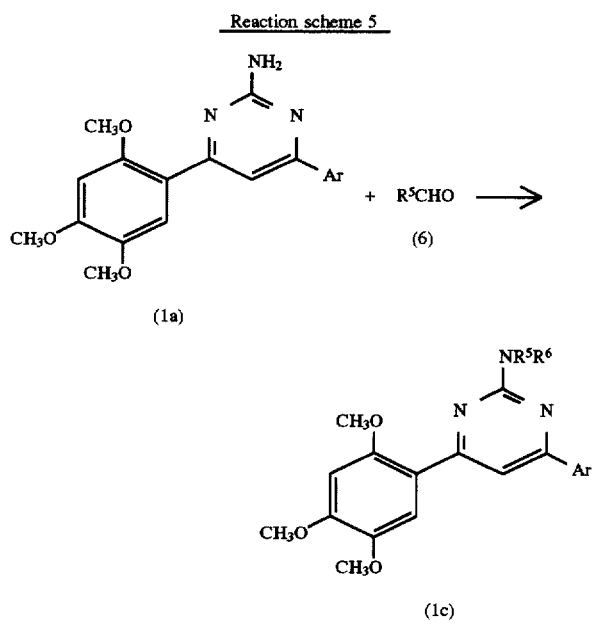

wherein Ar has the same meaning as defined above, $R^5$ and $R^6$ are the same or different and independently represents a hydrogen atom or lower alkyl group, with the proviso that $R^5$ and $R^6$ are not hydrogen atoms at the same time.

The target compound (1c) of the present invention can be obtained by reacting the compound represented by the formula (1a) and the compound represented by the formula (6) in a suitable solvent under hydrogen pressure in the presence of a reducing agent.

No particular limitation is imposed on the solvent insofar as it takes no part in the reaction. Examples of the solvent include alcohols such as methanol and ethanol, ethers such as ethyl ether and tetrahydrofuran, halogenated hydrocarbons such as methylene chloride and chloroform, aromatic hydrocarbons such as benzene and toluene, aprotic polar solvents such as N,N-dimethylformamide, dimethyl sulfoxide and acetonitrile, lower aliphatic carboxylic acids such as formic acid and acetic acid, and water. They may be used either singly or in combination.

Illustrative of the reducing agent include sodium boron hydride, sodium cyanoboron hydride, aluminum lithium hydride, Raney nickel and palladium-carbon.

As hydrogen pressure, 1–200 atmospheric pressure or so is preferred.

In this reaction, the compound represented by the formula (6) and the reducing agent may be used each in an amount of about 0.1–100 equivalents, preferably 0.1 to 10 equivalents relative to the compound represented by the formula (1a).

The reaction may be conducted at a temperature ranging from under ice cooling to the boiling point of the solvent or so, preferably under ice cooling to room temperature or so. The reaction time may be 0.1 hour to 96 hours, by which the reaction proceeds advantageously.

The target compound (1c) of the present invention can be obtained by reacting the compound represented by the formula (1a) and the compound represented by the formula (6) in a suitable solvent in the presence of an acid catalyst, isolating the reaction product as an imine and then allowing the above-exemplified reducing agent to act on the imine.

Examples of the acid catalyst include inorganic acids such as hydrochloric acid and sulfuric acid and organic acids such as trifluoroacetic acid, p-toluenesulfonic acid and benzenesulfonic acid.

No particular limitation is imposed on the solvent insofar as it takes no part in the reaction. Examples of the solvent include benzene and toluene. The reaction can be allowed to proceed advantageously by removing water by azeotropy.

In the above reaction, it is preferred to use the acid catalyst in an amount of about 0.01 to 1 equivalent, more preferably 0.01 to 0.5 equivalent, relative to the compound represented by the formula (1a).

The reaction may be conducted at a temperature ranging from under ice cooling to the b oiling point of the solvent or so. The reaction time may be about 0.1 to 96 hours, by which the reaction proceeds advantageously.

The compound represented by the formula (1c) can also be obtained by alkylating the compound represented by the formula (1a). The alkylating reaction is conducted by reacting with an alkylating agent in a suitable solvent in the presence of a base. No particular limitation is imposed on the solvent insofar as it takes no part in the reaction. Examples include alcohols such as methanol and ethanol, ethers such as ethyl ether and tetrahydrofuran, halogenated hydrocarbons such as methylene chloride and chloroform, aromatic hydrocarbons such as benzene and toluene, aprotic polar solvents such as N,N-dimethylformamide, dimethylsulfoxide and acetonitrile, and alkyl ketones such as acetone and methyl ethyl ketone. They may be used either singly or in combination. Illustrative of the base include organic amines such as pyridine, triethylamine and piperidine, alkali metal hydrides such as sodium hydride and potassium hydride, hydroxides of an alkali metal such as sodium hydroxide and potassium hydroxide, sodium acetate, potassium carbonate and sodium carbonate.

Exemplary alkylating agents include halogenated alkyls such as methyl iodide and ethyl bromide and sulfate ester such as dimethyl sulfate and diethyl sulfate.

In this reaction, it is preferred to use the alkylating agent and the base each in an amount of about 1–100 equivalents, preferably about 1–20 equivalents relative to the compound represented by the formula (1a).

The reaction may be conducted at a temperature ranging from under ice cooling to the boiling point of the solvent or so. The reaction time may be about 0.1 to 96 hours, preferably about 0.1–24 hours, by which the reaction proceeds advantageously.

In the compounds of the formula (1) obtained according to above Reaction formulas 1–5, when Ar has a phthaliminoyl-substituted lower alkoxyl group as a substituent, the phthaliminoyl-substituted lower alkoxyl group can be converted into an amino-substituted lower alkoxyl group by reacting the compound with hydrazine, for example, in a suitable solvent as needed. No particular limitation is imposed on the solvent insofar as it takes no part in the reaction. Examples include alcohols such as methanol and ethanol. In this reaction, it is preferred to use hydrazine in an amount of about 1–100 equivalents relative to the compound represented by the formula (1). The reaction may be conducted at a temperature ranging from under ice cooling to the boiling point of the solvent or so. The reaction time may be about 1 to 96 hours, by which the reaction proceeds advantageously.

In the compounds of the formula (1) obtained according to the Reaction schemes 1–5 or the above-described reaction, when Ar has an amino-substituted lower alkoxyl group as a substituent, the amino-substituted lower alkoxyl group can be converted into a mono- or dialkylamino-substituted lower alkoxyl group by conducting the reaction in a similar manner to the reaction scheme 5 as needed.

In the compounds of the formula (1) obtained according to the Reaction schemes 1–5, when Ar has a hydroxyl-substituted lower alkoxyl group as a substituent, the hydroxyl-substituted lower alkoxyl group can be converted into $R^7$-substituted lower alkoxyl group by reacting with a compound (7) represented by $R^7(CH_2)_lX$ in the presence of a base, for example, in a suitable solvent as needed. Here, $R^7$ represents a hydroxyl group, polyether group, amino group which may be substituted by 1-2 lower alkyl groups, amineoxide group which may be substituted by 1-2 lower alkyl groups or monocyclic or fused-ring nitrogen-containing heterocyclic group which may be substituted by 1-3 lower alkyl groups, X represents a halogen atom and l stands for 1-6. No particular limitation is imposed on the solvent insofar as it takes no part in the reaction. Examples of the solvent include alcohols such as methanol and ethanol, ethers such as ethyl ether and tetrahydrofuran, halogenated hydrocarbons such as methylene chloride and chloroform, alkyl ketones such as acetone and methyl ethyl ketone aromatic hydrocarbons such as benzene and toluene, aprotic polar solvents such as N,N-dimethylformamide, dimethylsulfoxide and acetonitrile, and water. They may be used either singly or in combination. Illustrative of the base include organic amines such as pyridine, triethylamine and piperidine, alkyl metal hydrides such as sodium hydride and potassium hydride, hydroxides of an alkali metal such as sodium hydroxide and potassium hydroxide, sodium acetate, potassium carbonate and sodium carbonate.

The compound represented by the formula (7) is a salt with an acid compound, it is possible to neutralize the salt with a base, extract with an organic solvent and then add the extract directly to the reaction system.

The compound represented by the formula (7) and the base may be added each in an amount of about 1-100 equivalents, preferably 1-20 equivalents, relative to the compound represented by the formula (1). The reaction may be conducted at a temperature ranging from under ice cooling to the boiling point of the solvent or so. The reaction time may be about 0.1 to 96 hours, preferably 0.1-24 hours, by which the reaction proceeds advantageously.

When Ar is a compound having a hydroxyl group as a substituent, the substituent can be converted into a phosphate ester group by reacting with phosphorus oxychloride, for example, in pyridine.

In the above reaction, it is preferred to add phosphorus oxychloride in an amount of about 1-10 equivalents, preferably about 1-1.5 equivalents relative to the compound represented by the formula (1). The reaction may be conducted at a temperature ranging from under ice cooling to the boiling point of the solvent or so, with a temperature ranging from under ice cooling to room temperature or so being more preferred. The reaction time may be about 0.1 hour to 48 hours, preferably about 0.1 hour to 2 hours, by which the reaction proceeds advantageously.

In the compounds of the formula (1) obtained according to the Reaction formulas 1-5, when Ar has an amine as a substituent, it is possible to convert the compound into an amineoxide-containing compound by reacting with an oxidizing agent, for example, in a suitable solvent as needed. No particular limitation is imposed on the solvent insofar as it takes no part in the reaction. Examples of the solvent include ethers such as ethyl ether and tetrahydrofuran, halogenated hydrocarbons such as methylene chloride and chloroform, alkyl ketones such as acetone and methyl ethyl ketone, alcohols such as methanol and ethanol, aprotic polar solvents such as N,N-dimethylformamide, dimethylsulfoxide and acetonitrile, acetic acid and water. They may be used either singly or in combination. There is no particular limitation imposed on the oxidizing agent, however, examples include peroxides such as manganese dioxide, sodium hypochlorite, CAN (dicerium ammonium nitrate), DDQ (2,3-dichloro-5,6-dicyano-1,4-benzoquinone), chloranil (2,3,5,6-tetrachloro-1,4-benzoquinone), DMSO-pyridine sulfur trioxide complex, Jones' reagent, pyridinium chlorochromate, pyridinium dichromate, dimethylsulfoxide-oxalyl chloride, hydrogen peroxide and tert-butylhydroperoxide; and peracids such as performic acid, peracetic acid and methachloroperbenzoic acid. They may be used in combination.

In the above reaction, it is preferred to add an oxidizing agent in an amount of about 1-100 equivalents, preferably about 1-10 equivalents relative to the compound represented by the formula (1). The reaction may be conducted at a temperature ranging from under ice cooling to the boiling point of the solvent or so. The reaction time may be about 0.1 to 96 hours, preferably 0.1-1 hour, by which the reaction proceeds advantageously.

The compounds represented by the formulas (2)-(7) which are used as raw materials for the above reaction can be prepared using easily available compounds which are known to date or can be synthesized in a manner known to date. Alternatively, they can be prepared according to the Reaction schemes 6-9 which will be described below.

Reaction scheme 6

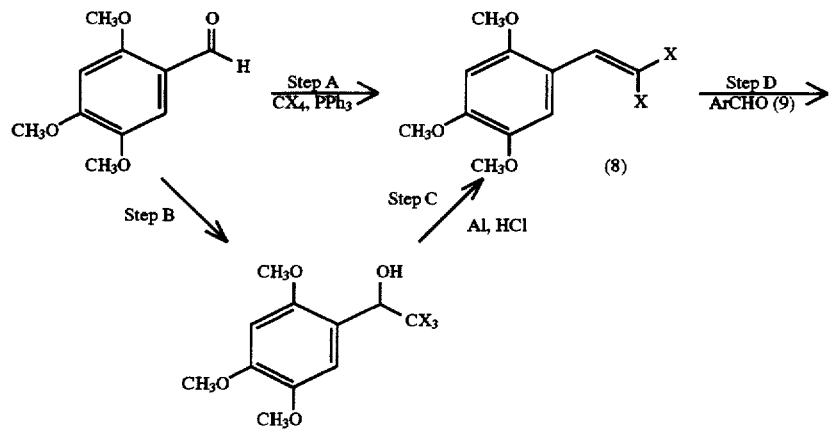

-continued
Reaction scheme 6

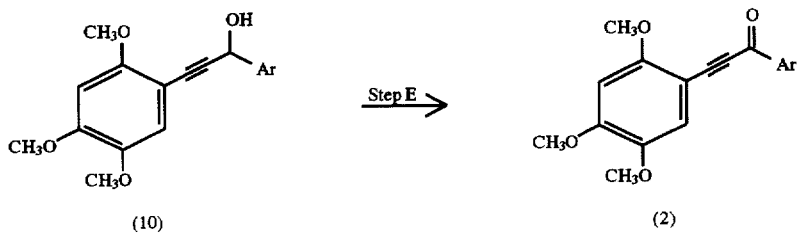

wherein Ar and X have the same meanings as defined above.
(Step A)

The compound represented by the formula (8) can be obtained by adding, in a suitable solvent, 2,4,5-trimethoxybenzaldehyde to the solvent which has been reacted with carbon tetrahalide and triphenylphosphine. No particular limitation is imposed on the solvent insofar as it takes no part in the reaction. Examples include halogenated hydrocarbons such as methylene chloride and chloroform.

In the above reaction, carbon tetrahalide is added in an amount of about 2–5 equivalents, preferably about 2–3 equivalents and triphenylphosphine is added in an amount of about 4–10 equivalents, preferably about 4–6 equivalents, each relative to 2,4,5-trimethoxybenzaldehyde. The reaction temperature may range from about −40° C. to room temperature, preferably about −20° C. to 0° C. The reaction time may be about 0.1 to 48 hours, preferably about 0.1 to 2 hours, by which the reaction proceeds advantageously.
(Step B)

By reacting 2,4,5-trimethoxybenzaldehyde with sodium trihaloacetate or a catalytic amount of lead bromide, aluminum and carbon tetrahalide in the presence of a solvent, 1-(1-hydroxy-2,2,2-trihaloethyl)-2,4,5-trimethoxybenzene can be obtained.

No particular limitation is imposed on the solvent insofar as it takes no part in the reaction. Examples of the solvent include alcohols such as methanol and ethanol, ethers such as ethyl ether and tetrahydrofuran, halogenated hydrocarbons such as methylene chloride and chloroform, alkyl ketones such as acetone and methyl ethyl ketone, aromatic hydrocarbons such as benzene and toluene, aprotic polar solvents such as N,N-dimethylformamide, dimethylsulfoxide and acetonitrile, and water. They may be used either singly or in combination. For the reaction, it is preferred to add lead bromide in an amount of about 0.01 to 1 equivalent and sodium trihaloacetate, aluminum and carbon tetrahalide each in an amount of about 1–10 equivalents, preferably about 1–2 equivalents, relative to 2,4,5-trimethoxybenzaldehyde.

The reaction may be conducted at a temperature ranging from under ice cooling to the boiling point of the solvent or so. The reaction time may be about 0.1–96 hours, preferably about 0.1–24 hours, by which the reaction proceeds advantageously.
(Step C)

The compound represented by the formula (8) can be obtained by reacting 1-(1-hydroxy-2,2,2-trihaloethyl)-2,4,5-trimethoxybenzene with aluminum and hydrochloric acid in the presence of a solvent.

No particular limitation is imposed on the solvent insofar as it takes no part in the reaction. Examples include alcohols such as methanol and ethanol, ethers such as ethyl ether and tetrahydrofuran, halogenated hydrocarbons such as methylene chloride and chloroform, alkyl ketones such as acetone and methyl ethyl ketone, aromatic hydrocarbons such as benzene and toluene, aprotic polar solvents such as N,N-dimethylformamide, dimethylsulfoxide and acetonitrile, and water. They may be used either singly or in combination.

In the above reaction, it is preferred to use hydrochloric acid in an amount of about 0.01–100 equivalents, preferably about 0.1–3 equivalents and aluminum in an amount of about 1–100 equivalents, preferably about 1–5 equivalents relative to 1-(1-hydroxy-2,2,2-trihaloethyl)-2,4,5-trimethoxybenzene. The reaction may be conducted at a temperature ranging from under ice cooling to the boiling point of the solvent or so. The reaction time may be about 0.1 to 96 hours, preferably about 0.1 to 24 hours, by which the reaction proceeds advantageously.

It is also possible to add a metal halide represented by $MetX_n$ (Met represents a metal such as nickel, tin, zinc, cerium, aluminum, silver, mercury, copper, lead or iron, X represents a halogen atom and n stands for 1–3) to promote the reaction.
(Step D)

The compound represented by the formula (10) can be obtained by reacting the compound represented by the formula (8) with a base in a suitable solvent optionally under an inert gas atmosphere, followed by the reaction with the compound represented by the formula (9).

When Ar has a hydroxyl group as a substituent, reaction can be conducted after the hydroxyl group is protected with a suitable protective group. No particular limitation is imposed on the protective group insofar as it exerts no influence upon removal of the protective group by the deblocking reaction which will be conducted later. Examples of the protective group usable here include methoxyethoxymethyl, methoxymethyl, tetrahydrofuranyl, tetrahydropyranyl, benzyl, p-methoxybenzyl, tertbutyldimethylsilyl and diphenylmethylsilyl groups. The introduction of the protective group can be conducted in accordance with the method described in "Protective Groups in Organic Synthesis, 2nd edition 14–174(1991)".

No particular limitation is imposed on the solvent insofar as it takes no part in the reaction. Examples include ethers such as ethyl ether and tetrahydrofuran, halogenated hydrocarbons such as methylene chloride and chloroform, aromatic hydrocarbons such as benzene and toluene, and alcohols such as methanol and ethanol. There is no particular limitation imposed on the inert gas insofar as it takes no part in the reaction. Examples include nitrogen and argon. Illustrative of the base include alkyl lithium compounds such as methyl lithium and n-butyl lithium, organic magnesium compounds such as ethyl magnesium bromide and isopropyl magnesium bromide; alkali metal hydrides such as sodium hydride and potassium hydride; and hydroxides of an alkali metal such as sodium hydroxide and potassium hydroxide.

In the above reaction, it is preferred to use the base in an amount of about 2–10 equivalents, preferably about 2–3 equivalents and the compound represented by the formula (9) in an amount of about 1–2 equivalents, preferably 1–1.2 equivalents, each relative to the compound represented by the formula (8). The reaction temperature may range from about –78° C. to room temperature in the reaction with the base and about –40° C. to 50° C. in the reaction with the compound represented by the formula (9). The reaction time may range from about 0.1 hour to 48 hours, preferably about 0.1 hour to 2 hours in the reaction with the base and about 0.1 hour to 48 hours, preferably about 0.1 hour to 2 hours in the reaction with the compound represented by the formula (9), by which the reaction proceeds advantageously.

The compound represented by the formula (10) in the above reaction can be purified as needed or can be provided for the next step without purification as needed.

(Step E)

The compound represented by the formula (2)can be obtained by reacting the compound represented by the formula (10) with an oxidizing agent in a suitable solvent.

No particular limitation is imposed on the solvent insofar as it takes no part in the reaction. Examples include ethers such as ethyl ether and tetrahydrofuran, halogenated hydrocarbons such as methylene chloride and chloroform, alkyl ketones such as acetone and methyl ethyl ketone, alcohols such as methanol and ethanol, aprotic polar solvents such as N,N-dimethylformamide, dimethylsulfoxide and acetonitrile, acetic acid and water. They may be used either singly or in combination. There is no particular limitation is imposed on the oxidizing agent, however, examples include metal oxides represented by Met$_m$O$_n$ (Met represents a metal such as manganese, nickel, tungsten, chromium, vanadium, titanium, silver, mercury, copper, lead or iron, m stands for 1–3 and n stands for 1–3), peroxides such as sodium hypochlorite, CAN (dicerium ammonium nitrate), DDQ (2,3-dichloro-5,6-dicyano-1,4-benzoquinone), chloranil (2,3,5,6-tetrachloro-1,4-benzoquinone), DMSO-pyridine sulfur trioxide complex, Jones' reagent, pyridinium chlorochromate, pyridinium dichromate, dimethylsulfoxide-oxalyl chloride, hydrogen peroxide and tert-butylhydroperoxide; and peracids such as performic acid, peracetic acid and methachloroperbenzoic acid. They may be used in combination.

In the above reaction, it is preferred to add an oxidizing agent in an amount of about 1–100 equivalents, preferably about 1–10 equivalents relative to the compound represented by the formula (10). The reaction may be conducted at a temperature ranging from under ice cooling to the boiling point of the solvent or so. The reaction time may be about 0.1 to 96 hours, preferably about 0.5–12 hours, by which the reaction proceeds advantageously.

The compound represented by the formula (2') can also be obtained by using the compound represented by the formula (9) instead of 2,4,5-trimethoxybenzaldehyde and 2,4,5-trimethoxybenzaldehyde instead of the compound represented by the formula (9) and conducting the reaction similar to the Reaction scheme 6.

The compound represented by the formula (9) can be prepared using a compound known to date or in a manner known to date. For example, in the compound represented by the formula (9), when Ar has a hydroxyl group as a substituent, it can be converted into a lower alkoxyl group which may be substituted by R$^7$ by reacting with the compound (7) represented by R$^7$(CH$_2$)$_l$X optionally in the presence of a base, for example, in a suitable solvent. In the formula, R$^7$, l and X have the same meanings as defined above. No particular limitation is imposed on the solvent insofar as it takes no part in the reaction. Examples include alcohols such as methanol and ethanol, ethers such as ethyl ether and tetrahydrofuran, halogenated hydrocarbons such as methylene chloride and chloroform, alkyl ketones such as acetone and methyl ethyl ketone, aromatic hydrocarbons such as benzene and toluene, aprotic polar solvents such as N,N-dimethylformamide, dimethylsulfoxide and acetonitrile, and water. They may be used either singly or in combination. Illustrative of the base include organic amines such as pyridine, triethylamine and piperidine, alkyl metal hydrides such as sodium hydride and potassium hydride, hydroxides of an alkali metal such as sodium hydroxide and potassium hydroxide, sodium acetate, potassium carbonate and sodium carbonate.

When the compound represented by the formula (7) is a salt with an acidic compound, it is also possible to add a base to the salt for neutralization, extract with an organic solvent and then add the extract directly to the reaction system.

In the above reaction, it is preferred to use the compound represented by the formula (7) and a base each in an amount of about 1–100, preferably about 1–20 equivalents relative to the compound represented by the formula (9). The reaction may be conducted at a temperature ranging from under ice cooling to the boiling point of the solvent or so. The reaction time may be about 0.1–96 hours, preferably about 0.1–24 hours, by which the reaction proceeds advantageously.

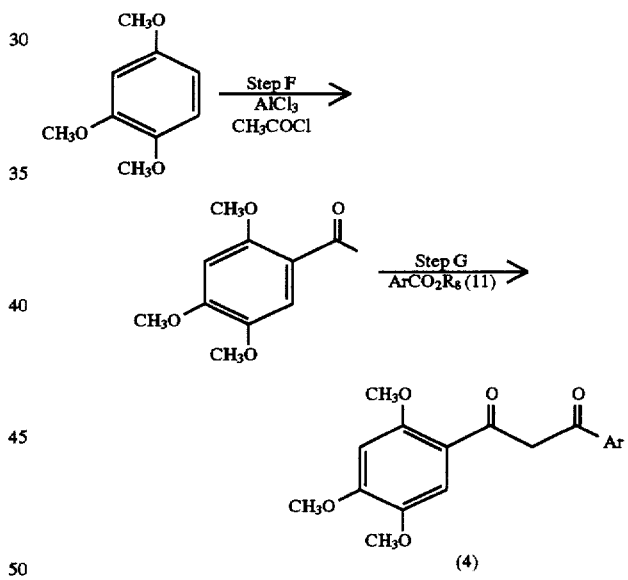

wherein Ar and R have the same meanings as defined above and R$^8$ represents a lower alkyl group.

(Step F)

By reacting 2,4,5-trimethoxybenzene with aluminum chloride in a suitable solvent and then with acetyl chloride, 2',4'-5'-trimethoxyacetophenone can be obtained.

No particular limitation is imposed on the solvent insofar as it takes no part in the reaction. Examples include halogenated hydrocarbons such as methylene chloride and chloroform, aromatic hydrocarbons such as benzene and toluene, and carbon disulfide.

For the reaction, it is preferred to use aluminum chloride in an amount of about 1–100 equivalents, preferably about 1–5 equivalents, relative to 2,4,5-trimethoxybenzene. The reaction may be conducted at a temperature ranging from under ice cooling to the boiling point of the solvent or so, preferably under ice cooling to room temperature or so. The reaction time may about 0.1–96 hours, preferably about 0.5–24 hours, by which the reaction proceeds advantageously.

(Step G)

The compound represented by the formula (4) can be obtained by reacting 2',4',5'-trimethoxyacetophenone with the compound represented by the formula (11) in the presence of a base in a suitable solvent.

No particular limitation is imposed on the solvent insofar as it takes no part in the reaction. Examples of the solvent include alcohols such as methanol and ethanol, ethers such as ethyl ether and tetrahydrofuran, halogenated hydrocarbons such as methylene chloride and chloroform, aromatic hydrocarbons such as benzene and toluene, aprotic polar solvents such as N,N-dimethylformamide, dimethylsulfoxide and acetonitrile, and water.

Illustrative of the base include organic amines such as pyridine, triethylamine and piperidine, alkoxides of an alkali metal such as sodium methoxide, sodium ethoxide, potassium tert-butoxide and sodium isopropoxide, alkyl lithium compounds such as n-butyl lithium and tert-butyl lithium, organic magnesium compounds such as ethyl magnesium bromide and isopropyl magnesium bromide, alkali metal hydrides such as sodium hydride and potassium hydride, hydroxides of an alkali metal such as sodium hydroxide and potassium hydroxide, sodium acetate, potassium carbonate, sodium carbonate and lithium diisopropylamine.

In the above reaction, it is preferred to use the base and the compound represented by the formula (11) each in an amount of about 1–20 equivalents, preferably about 1–5 equivalents relative to 2',4',5'-trimethoxyacetophenone. The reaction may be conducted at a temperature ranging from about −78° C. to the boiling point of the solvent. The reaction time may be about 0.1 to 96 hours, preferably about 0.5 to 24 hours, by which the reaction proceeds advantageously.

The compound represented by the formula (4) can also be obtained by using the compound (12) represented by the formula ArCOCH$_3$ instead of 2',4',5'-trimethoxyacetophenone and a lower alkyl ester of 2,4,5-trimethoxybenzoic acid instead of the compound represented by the formula (11) and then conducting the reaction similar to the Reaction scheme 7.

Reaction scheme 8

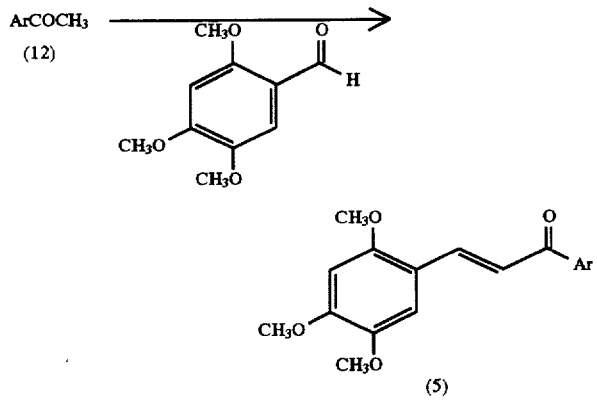

wherein Ar has the same meaning as defined above.

The compound represented by the formula (5) can be obtained by reacting the compound represented by the formula (12) with 2,4,5-trimethoxybenzaldehyde in the presence of a base in a suitable solvent.

No particular limitation is imposed on the solvent insofar as it takes no part in the reaction. Examples include alcohols such as methanol and ethanol, ethers such as ethyl ether and tetrahydrofuran, aromatic hydrocarbons such as benzene and toluene and aprotic polar solvents such as N,N-dimethylformamide, dimethylsulfoxide and acetonitrile. Illustrative of the base include organic amines such as pyridine, triethylamine and piperidine, alkoxides of an alkali metal such as sodium methoxide, sodium ethoxide, potassium tert-butoxide and sodium isopropoxide, alkali metal hydrides such as sodium hydride and potassium hydride, and hydroxides of an alkali metal such as sodium hydroxide and potassium hydroxide, sodium acetate, potassium carbonate and sodium carbonate.

In the above reaction, it is preferred to use the base in an amount of about 1–100 equivalents, preferably about 1–5 equivalents, and 2,4,5-trimethoxybenzaldehyde in an amount of about 1–5 equivalents, preferably about 1–1.2 equivalents, relative to the compound represented by the formula (12).

The reaction may be conducted at a temperature ranging from under ice cooling to the boiling point of the solvent or so. The reaction time may be about 0.1 to 96 hours, preferably about 1–24 hours, by which the reaction proceeds advantageously.

Here, the compound represented by the formula (12) which has a methanesulfoamide group as a substituent can be synthesized by using as a raw material the compound represented by the formula (12) which has an amine group as a substituent and reacting it with a lower alkyl sulfonyl chloride in a suitable solvent.

No particular limitation is imposed on the solvent insofar as it takes no part in the reaction. Examples of the solvent include alcohols such as methanol and ethanol, ethers such as ethyl ether and tetrahydrofuran, halogenated hydrocarbons such as methylene chloride and chloroform, aromatic hydrocarbons such as benzene and toluene and aprotic polar solvents such as N,N-dimethylformamide, dimethylsulfoxide and acetonitrile. To accelerate the reaction, an organic amine such as pyridine, dimethylaminopyridine or triethylamine can be added. If the organic amine is in the liquid form, the base can be used directly as a solvent.

The reaction proceeds advantageously even by adding a condensing agent such as N,N'-dicyclohexylcarbodiimide, ethyl chlorocarbonate, pivaloyl chloride or chlorosulfonyl isocyanate.

In the above reaction, it is preferred to use methanesulfonyl chloride in an amount of about 1–10 equivalents, preferably about 1–2 equivalents relative to the compound represented by the formula (12) which has an amino group as a substituent. The reaction may be conducted at a temperature ranging from under ice cooling to the boiling point of the solvent or so, preferably from under ice cooling to room temperature or so. The reaction time may be about 0.1 to 96 hours, by which the reaction proceeds advantageously.

The compound represented by the formula (5') can be obtained by using 2',4',5'-trimethoxyacetophenone instead of the compound represented by the formula (12) and the compound represented by the formula (9) instead of 2,4,5-trimethoxybenzaldehyde and conducting the reaction similar to the Reaction scheme 8.

Reaction scheme 9

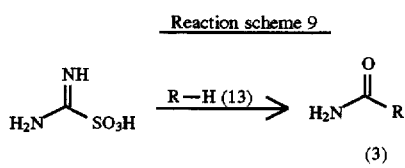

(3)

wherein R has the same meaning as defined above.

The compound represented by the formula (3) can be obtained by reacting aminoiminomethanesulfonic acid with the compound represented by the formula (13) in a suitable solvent.

No particular limitation is imposed on the solvent insofar as it takes no part in the reaction. Examples of the solvent include alcohols such as methanol and ethanol, ethers such as ethyl ether and tetrahydrofuran, halogenated hydrocarbons such as methylene chloride and chloroform, aromatic hydrocarbons such as benzene and toluene and aprotic polar solvents such as N,N-dimethylformamide, dimethylsulfoxide and acetonitrile.

In the above reaction, it is preferred to use the compound represented by the formula (13) in an amount of about 1–10 equivalents, preferably about 1–2 equivalents, relative to aminoiminomethanesulfonic acid. The reaction may be conducted at a temperature ranging from under ice cooling to the boiling point of the solvent or so, preferably from room temperature to 50° C. or so. The reaction time may be about 0.1 to 96 hours, preferably about 0.5–24 hours, by which the reaction proceeds advantageously.

The compound represented by the formula (3) can also be used as is for the subsequent reaction without purification. Alternatively, a protonic acid is added to the compound for isolation. Examples of the protonic acid include hydrochloric acid, sulfuric acid, acetic acid, benzoic acid, picric acid, tartaric acid and methanesulfonic acid.

The compounds and the invention compounds obtained by the above methods can each be isolated and purified using conventional separating and purifying means known to date, for example, concentration, solvent extraction, filtration, recrystallization or chromatography.

The 4,6-diarylpyrimidine derivative according to the present invention has excellent neovascular inhibitory activity and can be use as an effective ingredient for a preventive and curative of various diseases caused by abnormal neovascular formation, particularly a preventive and curative for tumor, rheumatism, diabetic retinopathy or psoriasis.

The compound of the present invention can be converted into a pharmaceutical composition in a manner known to date by using a suitable carrier. As the carrier, various carriers generally used for the conventional drugs can be used. Examples include an excipient, binder, disintegrator, lubricant, colorant, taste corrigent, smell corrigent and surfactant.

There is no particular limitation imposed on the dosage unit form upon using the pharmaceutical of the present invention as a curative for mammary animals including human being. The dosage form can be selected as needed according to the purpose of the treatment. Specific examples include parenteral preparations such as injection, suppository, external preparation (ointment, plaster or the like) and aerosol; and oral preparations such as tablets, coated tablets, powders, granules, capsules, liquid preparations, pills, suspensions and emulsions.

The above-described various compositions can be prepared by the method known conventionally in this field.

Upon formation into oral solid preparations such as tablets, powders and granules, the following carriers can be used. Examples of the excipient include lactose, sucrose, sodium chloride, glucose, urea, starch, calcium carbonate, kaolin, crystalline cellulose, silicic acid, methyl cellulose, glycerin, sodium alginate and gum arabic; examples of the binder include single syrup, glucose solution, starch solution, gelatin solution, polyvinyl alcohol, polyvinyl ether, polyvinyl pyrrolidone, carboxymethyl cellulose, shellac, methyl cellulose, ethyl cellulose, water, ethanol and potassium phosphate; examples of the disintegrator include dry starch, sodium alginate, agar powder, laminaran powder, sodium bicarbonate, calcium carbonate, polyoxyethylene sorbitan fatty acid esters, sodium laurylsulfate, monoglyceride stearate, starch and lactose; examples of the disintegration inhibitor include sucrose, stearic acid, cacao butter and hydrogenated oil, examples of the absorption promoter include quaternary ammonium bases and sodium lauryl sulfate; examples of the humectant include glycerin and starch; examples of the adsorbent include starch, lactose, kaolin, bentonite and silicic acid in the colloid form; and examples of the lubricant include purified talc, stearate salts, boric acid powder and polyethylene glycol. To the tablet, general coating can be applied at need. Examples of the available tablet include sugar coated tablet, gelatin coated tablet, enteric coated tablet, film coated tablet, double layer tablet and multiple layer tablet.

Upon formation into the form of a pill, usable are the following carriers, for example, an excipient such as glucose, lactose, starch, cacao butter, hydrogenated plant oil, kaolin or talc sugar; a binder such as gum arabic power, gum tragacanth powder, gelatin or ethanol; and a disintegrator such as laminaran or starch.

Capsules can be prepared by filling a mixture with the above-exemplified various carriers in hard gelatin capsules, soft capsules or the like.

Upon formation into the suppository form, a suitable absorption promoter is added to as a carrier such as polyethylene glycol, cacao butter, lanolin, a higher alcohol, an ester of a higher alcohol, gelatin, semi-synthetic glyceride or "Witepsol" (trade mark, product of Dynamite Nobel).

Upon formation into the form of an injection, carriers employed are a diluent such as water, ethyl alcohol, macrogol, propylene glycol, ethoxylated isostearyl alcohol, polyoxylated isostearyl alcohol or polyoxyethylene sorbitan fatty acid ester; a pH regulator and buffer such as sodium citrate, sodium acetate or sodium phosphate; and a stabilizer such as sodium pyrosulfite, ethylenediaminetetraacetic acid, thioglycollic acid or thiolactic acid. Incidentally, it is possible to add to a pharmaceutical composition a salt, glucose or glycerin in an amount sufficient for the preparation of an isotonic solution. It is also possible to add a conventional solubilizing agent, smoothing agent, local anesthetic or the like. After the addition of such carriers, subcutaneous, intramuscular or intravenous injections can be prepared in a manner known per se in the art.

The liquid preparation can be an aqueous or oily suspension, solution, syrup or elixir and it is prepared in a manner known per se in the art by using a conventional additive.

Upon formation into an ointment, for example, formation in the form of a paste, cream or gel, a conventionally-employed base, stabilizer, wetting agent, preservative and the like are blended at need and formed into preparations in a manner Per se in the art. Examples of the base include white vaseline, paraffin, glycerin, cellulose derivative, polyethylene glycol, silicon and bentonite. Examples of the preservative include methyl paraoxybenzoate, ethyl paraoxybenzoate and propyl paraoxybenzoate.

Upon formation of a plaster, it is only necessary to apply the above-described ointment, cream, gel or paste on a conventional backing material in a manner known per se in the art. Examples of the suitable backing material includes woven fabrics of cotton, rayon or chemical fibers, nonwoven fabrics and films or foamed sheets of soft PVC, polyethylene or polyurethane.

The amount of the invention compound to be contained in the pharmaceutical composition according to the present invention differs with the dosage form, administration route, administration plan or the like and cannot be determined in a wholesale manner. It can be chosen suitably from a wide range but an amount of about 1–70 wt. % in the composition is preferred.

No particular limitation is imposed on the administration method of the pharmaceutical of the present invention. The administration method can be suitably chosen from intestinal administration, oral administration, rectal administration, intraoral administration or subcutaneous administration depending on the form of the composition, age and sex of each patient, other conditions, degree of symptoms of the patient. For example, tablets, pills, liquid preparations, suspensions, emulsions, granules and capsules are orally administered, while suppositories are for rectal administration. The injection can be intravenously administered either singly or after mixed with a conventional fluid replacement such as glucose or amino acid. Furthermore, it is administered singly as needed through an intraarterial, intramuscular, intracutaneous, subcutaneous or intraperitoneal route. The ointment is applied to the skin, oral mucosa or the like.

The dosage of the compound of the present invention can be suitably chosen depending on the usage, age, sex and condition of each patient, the kind of the invention compound to be administered and other conditions, but it is preferred to administer the compound in an amount falling within a range of about 0.1–1000 mg/kg per day, preferably 0.5–100 mg/kg per day, as a standard amount. The pharmaceutical of the present invention can be administered once or 2–4 portions a day.

EXAMPLES

The present invention will hereinafter be described more specifically by referential examples, examples and pharmacological tests. I should however be borne in mind that the present invention is not limited to or by the following examples.

Referential Example 1

Under ice cooling, to a 200 ml solution of 105 g of triphenyl phosphine in methylene chloride, a 100 ml solution of 67 g of carbon tetrabromide in methylene chloride were added dropwise. After stirring for five minutes, a 70 ml solution of 20 g of 2,4,5-trimethoxybenzaldehyde in methylene chloride were added dropwise to the reaction mixture. After the completion of the dropwise addition, stirring was conducted for one hour. Water was added to the reaction mixture, followed by extraction with methylene chloride. The extract was washed with saturated saline and dried over anhydrous magnesium sulfate. The organic layer was concentrated under reduced pressure. The residue was separated and purified by chromatography on a silica gel column (developing solvent, ethyl acetate: n-hexane), whereby 31.2 g of 2',2'-dibromoethylene-2,4,5-trimethoxybenzene were obtained (yield 87%).

Melting point: 71°–71.5° C. $^1$H-NMR (CDCl$_3$)δ: 3.82 (3H,s), 3.85(3H,s), 3.91(3H,s), 6.48(1H,s), 7.39(1H,s), 7.60 (1H,s).

Referential Example 2

In 1.2 l of dimethylformamide, 196 g of 2,4,5-trimethoxybenzaldehyde were dissolved, followed by the addition of 241 g of sodium trichloroacetate salt under ice cooling. The resulting mixture was stirred at room temperature for 9 hours. After the reaction, 2 l of water were added to the reaction mixture under ice cooling. The solid so precipitated was collected by filtration, followed by washing with water and diethyl ether, whereby 272 g of 1-(1-hydroxy-2,2,2-trichloroethyl)-2,4,5-trimethoxybenzene were obtained (yield: 86%).

Melting point: 162.5°–164° C. $^1$H-NMR (CDCl$_3$)δ: 3.86 (3H,s), 3.87(3H,s), 3.91(3H,s), 3.96(1H,d,J=6.3Hz), 5.56 (1H,d,J=6.3Hz), 6.53(1H,s), 7.15(1H,s).

Referential Example 3

In 50 ml of dimethylformamide, 0.37 g of lead bromide, 0.41 g of aluminum foil and 1.96 g of 2,4,5-trimethoxybenzaldehyde were added, followed by the addition of 1.9 ml of carbon tetrachloride at room temperature. The resulting mixture was stirred for one hour. After the completion of the reaction, 2N hydrochloric acid was added to the reaction mixture under ice cooling, followed by extraction with ethyl acetate. The extract was washed successively with a saturated aqueous solution of sodium bicarbonate, water and saturated saline, followed by drying over anhydrous sodium sulfate. The solvent was distilled off under reduced pressure and the crude product so obtained was washed with methanol, whereby 2.49 g of 1-(1-hydroxy-2,2,2-trichloroethyl)-2,4,5-trimethoxybenzene were obtained (yield: 79%). The physical properties of the product were equal to those of the product obtained in Referential Example 2.

Referential Example 4

In 100 ml of methanol, 31.5 g of 1-(1-hydroxy-2,2,2-trichloroethyl)-2,4,5-trimethoxybenzene, which had been obtained in Referential Example 2 or 3, were dissolved, followed by the addition of 4.05 g of powdery aluminum and 1.4 ml of concentrated hydrochloric acid. The resulting mixture was heated under reflux for 12 hours. After the completion of the reaction, water was added to the reaction mixture, followed by extraction with diethyl ether. The extract was washed successively with 1N hydrochloric acid, a saturated aqueous solution of sodium bicarbonate, water and saturated saline, followed by drying over anhydrous sodium sulfate. The solvent was distilled off under reduced pressure, whereby 26.2 g of 2',2'-dichloroethylene-2,4,5-trimethoxybenzene were obtained (yield: 100%).

Melting point: 52°–55° C. Boiling point: 134°–136° C./0.3 mmHg $^1$H-NMR (CDCl$_3$)δ: 3.83(3H,s), 3.85(3H,s), 3.91(3H,s), 6.49(1H,s), 7.06(1H,s), 7.39(1H,s).

Referential Example 5 (alternative method for Referential Example 4)

In 15 ml of methanol, 2.4 g of 1-(1-hydroxy-2,2,2-trichloroethyl)-2,4,5-trimethoxybenzene were dissolved, followed by the addition of 0.14 g of lead bromide, 0.31 g of powdery aluminum and 1.2 ml of concentrated hydrochloric acid. The resulting mixture was stirred for one hour at room temperature. After the completion of the reaction, diethyl ether was added to the reaction mixture. The resulting mixture was washed with water and saturated saline and then dried over anhydrous sodium sulfate. The solvent was distilled off under reduced pressure, whereby 1.78 g of 2',2'-dichloroethylene-2,4,5-trimethoxybenzene were obtained (yield: 89%). The physical properties of the product were equal to those of the product obtained in Referential Example 4.

Referential Example 6

In 100 ml of dimethylformamide, 20 g of parahydroxybenzaldehyde, 100 g of dibromoethane and 40 g of potassium carbonate were added, followed by stirring under heat at 50° C. for 24 hours. After the completion of the reaction, water was added to the reaction mixture. The resulting mixture was extracted with ethyl acetate. The extract was washed with a 2N aqueous solution of sodium hydroxide and saturated saline, followed by drying over anhydrous magnesium sulfate. The organic layer was concentrated under reduced pressure. The residue was then separated and purified by chromatography on a silica gel column (developing solvent, ethyl acetate: n-hexane), whereby 15.4 g of 4-(2-bromoethoxy)benzaldehyde were obtained (yield: 38%).

Melting point: 49.5°–50° C. $^1$H-NMR (CDCl$_3$)δ: 3.67 (2H,t,J=6.2Hz), 4.38(2H,t,J=6.2Hz), 7.03(2H,d,J=11.3Hz), 7.86(2H,d,J=11.3Hz), 9.90(1H,s).

Referential Example 7

In 100 ml of tetrahydrofuran, 5.0 g of 4-(2-bromoethoxy) benzaldehyde obtained in Referential Example 6, 2.2 g of N-methyl piperazine and 2.5 g of dimethylaminopyridine were added, followed by heating under reflux for 24 hours. After the completion of the reaction, a 2N aqueous solution of sodium hydroxide was added to the reaction mixture. The resulting solution was then extracted with chloroform. The extract was washed with saturated saline, followed by drying over anhydrous magnesium sulfate. The organic layer was concentrated under reduced pressure, whereby 4.5 g of 4-(2-(4-methylpiperazinyl)ethoxy)benzaldehyde were obtained (yield: 52%).

Referential Example 8

In a 100 ml solution of 10 g of 2',2'-dibromoethylene-2,4,5-trimethoxybenzene, which had been obtained in Referential Example 1, in tetrahydrofuran, 20 ml of 1.6M n-butyl lithium were added at −78° C. under a nitrogen atmosphere. The temperature was then increased to room temperature. To the resulting mixture, a 20 ml solution of 2.7 g of methyl paraformylbenzoate in tetrahydrofuran was added, followed by stirring at room temperature for 2 hours. After the completion of the reaction, a saturated aqueous solution of ammonium chloride was added to the reaction mixture. The resulting mixture was extracted with ethyl acetate. The extract was washed with saturated saline and then dried over anhydrous magnesium sulfate. The organic layer was concentrated under reduced pressure. The concentrate was then recrystallized from n-hexane-ethyl acetate, whereby 8.2 g of 1-(4-methoxycarbonylphenyl)-3-(2,4,5-trimethoxyphenyl)-1-hydroxypropyl-2-nyl were obtained (yield: 79%).

Melting point: 128°–130° C. $^1$H-NMR (CDCl$_3$)δ: 2.43 (1H,d,J=6.1Hz), 3.83(3H,s), 3.91(3H,s), 3.93(3H,s), 5.78 (1H,d,J=6.1Hz), 6.49(1H,s), 6.91(1H,s), 7.74(2H,d,J=8.3Hz), 8.0(2H,d,J=8.3Hz).

Referential Example 9

In 300 ml of methylene chloride, 8.2 g of 1-(4-methoxycarbonylphenyl)-3-(2,4,5-trimethoxyphenyl)-1-hydroxypropyl-2-nyl which had been obtained in Referential Example 8 were dissolved, followed by the addition of 50 g of activated manganese dioxide. The resulting mixture was stirred at room temperature for 3 hours. After the activated manganese dioxide was filtered off, the filtrate was concentrated under reduced pressure. To the residue so obtained, n-hexane-ethyl acetate was added to precipitate crystals, whereby 7.6 g of 1-(4-methoxycarbonylphenyl)-3-(2,4,5-trimethoxyphenyl)-2-propynyl-1-one were obtained (yield: 93%).

Melting point: 137°–139° C. $^1$H-NMR (CDCl$_3$)δ: 3.87 (3H,s), 3.97(6H,s), 4.00(3H,s), 6.53(1H,s), 7.09(1H,s), 8.17 (2H,d,J=8.4Hz), 8.38(2H,d,J=8.4Hz).

Referential Example 10

In a similar manner to Referential Example 8 or 9, the compounds described below were obtained.

(a) 1,3-di(2,4,5-trimethoxyphenyl)-2-propynyl-1-one

Melting point: 177°–179° C. $^1$H-NMR (CDCl$_3$)δ: 3.86 (3H,s), 3.92(3H,s), 3.94(3H,s), 3.95(3H,s), 3.98(6H,s), 7.11 (1H,s), 7.50(1H,s), 7.54(1H,s), 7.78(1H,s).

(b) 1-(4-dimethylaminophenyl)-3-(2,4,5-trimethoxyphenyl)-2-propynyl-1-one

Melting point: 176.5°–178° C. $^1$H-NMR (CDCl$_3$)δ: 3.10 (6H,s), 3.86(3H,s), 3.95(3H,s), 3.97(3H,s), 6.52(1H,s), 6.69 (2H,d,J=9.2Hz), 7.09(1H,s), 8.19(2H,d,J=9.2Hz).

(c) 1-(4-dimethylaminonaphthyl)-3-(2,4,5-trimethoxyphenyl)-2-propynyl-1-one

Melting point: 104°–106° C. $^1$H-NMR (CDCl$_3$)δ: 3.03 (6H,s), 3.87(3H,s), 3.96(3H,s), 3.98(3H,s), 6.52(1H,s), 7.03 (1H,d,J=8.3Hz), 7.11(1H,s), 7.46–7.68(2H,m), 8.19(1H,d,J= 8.6Hz), 8.76(1H,d,J=8.2Hz), 9.44(1H,d,J=9.5Hz).

(d) 1-(3-pyridyl)-3-(2,4,5-trimethoxyphenyl)-2-propynyl-1-one

Melting point: 149°–151° C. $^1$H-NMR (CDCl$_3$)δ: 3.88 (3H,s), 3.97(3H,s), 4.00(3H,s), 6.53(3H,s), 7.09(3H,s), 7.46 (1H,dd,J=4.9,8.0Hz), 8.50(1H,ddd,J=2.0,2.0,8.0Hz), 8.82 (1H,dd,J=2.0,8.0Hz), 9.56(1H,d,J=2.0Hz).

(e) 1-(4-(2-dimethylaminoethyleneoxy)phenyl)-3-(2,4,5-trimethoxyphenyl)-2-propynyl-1-one Melting point: 47°–49° C. $^1$H-NMR (CDCl$_3$)δ: 2.36(6H, s), 2.77(2H,t,J=5.1Hz), 3.86(3H,s), 3.96(3H,s), 3.99(3H,s), 4.16(2H,t,J=5.6Hz), 6.52(1H,s), 7.00(2H,d,J=8.9Hz), 7.08 (1H,s), 8.27(2H,d,J=8.9Hz).

(f) 1-(3,5-dimethoxy-4-methoxyethoxymethoxyphenyl)-3-(2,4,5-trimethoxyphenyl)-2-propynyl-1-one Melting point: 94°–96° C. $^1$H-NMR (CDCl$_3$)δ: 3.37(3H, s), 3.51–3.59(2H,m), 3.86(3H,s), 3.93(3H,s), 3.94–4.03(2H, m), 3.95(6H,s), 3.96(3H,s), 5.31(2H,s), 6.52(1H,s), 7.11(1H, s), 7.61(2H,s).

(g) 1-(4-piperidylphenyl)-3-(2,4,5-trimethoxyphenyl)-2-propynyl-1-one

Melting point: 180°–183° C. $^1$H-NMR (CDCl$_3$)δ: 1.68 (6H,bs), 3.42(4H,bs), 3.86(3H,s), 3.95(3H,s), 3.97(3H,s), 6.52(1H,s), 6.88(2H,d,J=9.1Hz), 7.09(1H,s), 8.17(2H,d,J= 9.1Hz).

(h) 1-(4-chlorophenyl)-3-(2,4,5-trimethoxyphenyl)-2-propynyl-1-one

Melting point: 140°–142° C. $^1$H-NMR (CDCl$_3$)δ: 3.86 (3H,s), 3.96(3H,s), 3.97(3H,s), 6.52(1H,s), 7.07(1H,s), 7.47 (2H,d,J=8.6Hz), 8.24(2H,d,J=8.6Hz).

(i) 1-(2-nitrophenyl)-3-(2,4,5-trimethoxyphenyl)-2-propynyl-1-one

Melting point: 168°–170° C. $^1$H-NMR (CDCl$_3$)δ: 3.84 (3H,s), 3.89(3H,s), 3.94(3H,s), 6.90(1H,s), 6.98(1H,s), 7.63–7.74(2H,m), 7.84–7.87(2H,m), 7.99–8.02(2H,m).

(j) 1-(4-(2-bromoethyleneoxy)phenyl)-3-(2,4,5-trimethoxyphenyl)-2-propynyl-1-one Melting point: 113°–116° C. $^1$H-NMR (CDCl$_3$)δ: 3.68 (2H,t,J=6.2Hz), 3.86(3H,s), 3.96(3H,s), 3.98(3H,s), 4.39 (2H,t,J=6.2Hz), 6.52(1H,s), 6.99(2H,t,J=9.1Hz), 7.08(1H,s), 8.28(2H,t,J=9.1Hz).

(k) 1-(4-methoxyethoxymethoxyphenyl)-3-(2,4,5-trimethoxyphenyl)-2-propynyl-1-one Melting point: 77°–79° C. $^1$H-NMR (CDCl$_3$)δ: 3.38(3H, s), 3.51–3.58(2H,m), 3.79–3.89(2H,m), 3.87(3H,s), 3.96 (3H,s), 3.98(3H,s), 5.36(3H,s), 6.53(1H,s), 7.09(1H,s), 7.14 (2H,d,J=8.8Hz), 8.27(2H,d,J=8.8Hz).

(l) 1-(4-(4-methylpiperazinylethyleneoxy)phenyl)-3-(2,4,5-trimethoxyphenyl)-2-propynyl-1-one $^1$H-NMR (CDCl$_3$)δ: 2.30(3H,s), 2.48(4H,bs), 2.94(4H, bs), 2.86(2H,t,J=5.8Hz), 3.86(3H,s), 3.96(3H,s), 3.97(3H,s), 4.20(2H,d,J=5.8Hz), 6.52(1H,s), 6.98(2H,d,J=8.3Hz), 7.08 (1H,s), 8.26(2H,d,J=8.3Hz).

(m) 1-(2,4-dimethoxyphenyl)-3-(2,4,5-trimethoxyphenyl)-2-propynyl-1-one $^1$H-NMR (CDCl$_3$)δ: 3.85(3H,s), 3.89(3H,s), 3.94(3H,s), 6.45–6.60(3H,m), 7.07(1H,s), 8.29(1H,d,J=8.8Hz).

(n) 1-(2,4-dichlorophenyl)-3-(2,4,5-trimethoxyphenyl)-2-propynyl-1-one

Melting point: 143°–145° C. $^1$H-NMR (CDCl$_3$)δ: 3.85 (3H,s), 3.92(3H,s), 3.95(3H,s), 6.49(3H,s), 7.03(3H,s), 7.37 (1H,dd,J=2.0,8.6Hz), 7.49(1H,d,J=2.0Hz), 8.20(1H,d,J= 8.6Hz).

(o) 1-(2,5-dimethoxyphenyl)-3-(2,4,5-trimethoxyphenyl)-2-propynyl-1-one

Melting point: 62°–64° C. $^1$H-NMR (CDCl$_3$)δ: 3.82(3H, s), 3.88(3H,s), 3.93(3H,s), 6.47–6.58(3H,m), 7.08(1H,s), 8.28(1H,d,J=8.9Hz).

(p) 1-(3,4,5-trimetoxyphenyl)-3-(2,4,5-trimethoxyphenyl)-2-propynyl-1-one

Melting point: 168°–170° C. $^1$H-NMR (CDCl$_3$)δ: 3.86 (3H,s), 3.93(3H,s), 3.95(3H,s), 3.96(3H,s) 3.97(6H,s), 6.52 (1H,s), 7.10(1H,s), 7.61(2H,s).

Referential Example 11

Under ice cooling, 10.3 g of methanesulfonic acid chloride were added dropwise to a 120 ml solution of 15.6 g of 2'-amino-4',5'-dimethoxyacetophenone in pyridine, followed by stirring for 24 hours. After the solvent was concentrated under reduced pressure, water was added to the concentrate to precipitate crystals. The crystals so precipitated were collected by filtration, washed successively with water and ethanol and then dried, whereby 20.5 g of 2'-methanesulfoamide-4',5'-dimethoxyacetophenone were obtained (yield: 94%). In ethanol, 12.8 g of the compound so obtained and 9 g of 2,4,5-trimethoxybenzaldehyde were suspended, followed by the addition of 3.19 of sodium hydroxide. The resulting mixture was stirred at room temperature for 24 hours. The crystals so precipitated were collected by filtration and then dried, whereby 12.7 g of 1-(2'-methanesulfoamide-4',5'-dimethoxyphenyl)-3-(2,4,5-trimethoxyphenyl)-2-propenyl-1-one were obtained (yield: 60%).

Referential Example 12

In a similar manner to Referential Example 11, the compounds described below were obtained.

(q) 1-(4-Methylthiophenyl)-3-(2,4,5-trimethoxyphenyl)-2-propenyl-1-one

Melting point: 102°–104° C. $^1$H-NMR (CDCl$_3$)δ: 3.89 (3H,s), 3.92(3H,s), 3.96(3H,s), 6.54(1H,s), 7.23(2H,d,J= 8.6Hz), 7.38(1H,s), 7.52(2H,d,J=8.6Hz), 7.61(1H,s), 7.65 (1H,s).

(r) 1-(4-Thiazolyl)-3-(2,4,5-trimethoxyphenyl)-2-propenyl-1-one

Melting point: 175°–178° C. $^1$H-NMR (CDCl$_3$)δ: 3.91 (3H,s), 3.92(3H,s), 3.95(3H,s), 6.51(1H,s), 7.22(1H,s), 7.67 (1H,d,J=3.0Hz), 7.80(1H,d,J=16.0Hz), 8.04(1H,d,J=3.0Hz), 8.40(1H,d,J=16.0Hz).

Referential Example 13

To methylene chloride, 47.5 g of aluminum chloride were added, followed by the addition of 30 g of 2,4,5-trimethoxybenzene and then 13 ml of acetyl chloride under ice cooling. The resulting mixture was stirred at room temperature for 6 hours. After the completion of the reaction, 1N hydrochloric acid was added to the reaction mixture under ice cooling. The resulting mixture was then extracted with methylene chloride. The extract so obtained was washed successively with 1N hydrochloric acid, a 1N aqueous solution of sodium hydrochloride and saturated saline and then dried over anhydrous magnesium sulfate. The organic layer was concentrated under reduced pressure. The crude product so obtained was washed with ethanol, whereby 18.6 g of 2',4',5'-trimethoxyacetophenone were obtained (yield: 50%).

Melting point: 91°–93° C. $^1$H-NMR (CDCl$_3$)δ: 2.60(3H, s), 3.88(3H,s), 3.92(3H,s), 3.95(3H,s), 6.51(1H,s), 7.43(1H, s).

Referential Example 14

To 21.2 g of 2,4,5-trimethoxybenzoic acid, 30 ml of thionyl chloride were added at room temperature, followed by heating under reflux for 4 hours. The reaction mixture was thereafter distilled off under reduced pressure. To the residue so obtained, 50 ml of dichloromethane, 10 ml of methanol and 20 ml of triethylamine were added, followed by stirring under ice cooling for one hour. After the completion of the reaction, water was added to the reaction mixture, followed by extraction with chloroform. The extract was washed successively with 1N hydrochloric acid, a saturated aqueous solution of sodium bicarbonate, water and saturated saline and then dried over anhydrous sodium sulfate. The solvent was distilled off under reduced pressure, whereby a crude product was obtained. The crude product so obtained was washed with methanol, whereby 14.6 g of methyl 2,4,5-trimethoxybenzoate were obtained (yield: 65%).

Melting point: 91.5°–92.5° C. $^1$H-NMR (CDCl$_3$)δ: 3.88 (6H,s), 3.91(3H,s), 3.94(3H,s), 6.54(1H,s), 7.41(1H,s).

Referential Example 15

In 20 ml of dimethylformamide, 2.5 g of methyl 2,4,5-trimethoxybenzoate obtained in Referential Example 14 and 2.1 g of 2',4',5'-trimethoxyacetophenone obtained in Referential Example 13 were dissolved, followed by the addition of 0.8 g of 60% sodium hydride under ice cooling. The resulting mixture was stirred for one hour at room temperature and for one hour at 100° C. To the reaction mixture, water and ethyl acetate were added under ice cooling and yellow powders so precipitated were collected by filtration. The powders were washed with water and ethyl acetate, whereby 3.3 g of 1,3-di(2,4,5-trimethoxyphenyl)-1,3-propanedione were obtained (yield: 82%).

Melting point: 173°–176° C. $^1$H-NMR (CDCl$_3$)δ: 3.92 (6H,s), 3.96(12H,s), 6.55(2H,s), 7.58(2H,s), 7.61(1H,s).

Referential Example 16

In a similar manner to Referential Example 15, 1-(2,4,5-trimethoxyphenyl)-3-(3,4,5-trimethoxyphenyl)-1,3-propanedione was obtained.

Melting point: 154°–156° C. ¹H-NMR (CDCl₃)δ: 3.80 (6H,s), 3.91(6H,s), 3.94(3H,s), 4.01(3H,s), 6.83(1H,s), 7.24 (2H,s), 7.32(1H,s), 7.48(1H,s).

Referential Example 17

To 100 ml of dimethylformamide, 1.2 g of imidazole and 0.7 g of 60% sodium hydride were added and they were stirred at room temperature for 10 minutes. To the reaction mixture, 7.3 g of 1-(4-(2-bromoethyleneoxy)phenyl)-3-(2,4, 5-trimethoxyphenyl)-2-propynyl-1-one obtained in Referential Example 10(j) were added, followed by stirring for 24 hours. Water was added to the reaction mixture and the precipitate so obtained was collected by filtration. The precipitate so obtained was washed with water and methanol, whereby 3.0 g of 1-(4-(2-imidazoryl-ethyleneoxy)phenyl)-3-(2,4,5-trimethoxyphenyl)-2-propynyl-1-one were obtained (yield 43%).

Melting point: 143°–1460° C. ¹H-NMR (CDCl₃)δ: 3.86 (3H,s), 3.96(3H,s), 3.97(3H,s), 4.31(2H,d,J=4.8Hz), 4.39 (2H,d,J=4.8Hz), 6.52(1H,s), 6.96(2H,d,J=8.8Hz), 7.02–7.13 (2H,m), 7.62(1H,s), 8.27(2H,d,J=8.8Hz).

Referential Example 18

In a similar manner to Referential Example 17, 1-(4-(N-phthaliminoylethyleneoxy)phenyl)-3-(2,4,5-trimethoxyphenyl)-2-propynyl-1-one was obtained.

Melting point: 174°–176° C. ¹H-NMR (CDCl₃)δ: 3.86 (3H,s), 3.96(3H,s), 3.97(3H,s), 4.15(2H,d,J=5.7Hz), 4.30 (2H,d,J=5.7Hz), 6.52(1H,s), 6.96(2H,d,J=8.9Hz), 7.07(1H, s), 7.68–7.77(2H,m), 7.84–7.91(2H,m), 8.24(2H,d,J= 8.9Hz).

EXAMPLE 1

In 50 ml of dimethylformamide, 5.0 g of 1-(4-methoxycarbonylphenyl)-3-(2,4,5-trimethoxyphenyl)-2-propynyl-1-one obtained in Referential Example 9 were dissolved, followed by the addition of 1.27 g of sodium acetate and 2.1 g of 1,1-dimethylguanidine sulfate. The resulting mixture was stirred under heat at 150° C. for 12 hours. After the reaction mixture was allowed to cool down, water was added to precipitate crystals, whereby 2.6 g of Compound 1 shown in Table 1 were obtained (yield: 44%).

EXAMPLE 2

To a small amount of water, 0.18 g of potassium tertbutoxide and 0.2 g of 1,1-dimethylguanidine sulfate were added, followed by the addition of 20 ml of dimethylformamide and 0.5 g of 1,3-di(2,4,5-trimethoxyphenyl)-2-propynyl-1-one obtained in Referential Example 10(a). The resulting mixture was stirred under heat at 150° C. for 12 hours. After the reaction mixture was allowed to cool down, water was added to precipitate crystals, whereby 0.43 g of Compound 2 shown in Table 1 was obtained (yield: 73%).

IR(KBr)cm⁻¹: 606 679 756 811 860 896 954 1030 1085 1157 1181 1208 1244 1269 1304 1340 1348 1398 1412 1423 1440 1451 1458 1467 1515 1546 1548 1552 1556 1610 2838 2903 2937 3002

EXAMPLE 3

In a similar manner to Example 1 except that 1,3-di(2,4, 5-trimethoxyphenyl)-2-propynyl-1-one obtained in Referential Example 10(a) and guanidine carbonate were used as raw materials, Compound 3 shown in Table 1 was synthesized.

IR(KBr)cm⁻¹: 570 758 860 867 1031 1045 1197 1209 1220 1271 1309 1341 1350 1433 1443 1461 1518 1537 1554 1587 1609 1624 3370 3468

EXAMPLE 4

In a similar manner to Example 2 except that 1-(4-dimethylaminophenyl)-3-(2,4,5-trimethoxyphenyl)-2-propynyl-1-one obtained in Referential Example 10(b) and guanidine carbonate were used as raw materials, Compound 4 shown in Table 1 was synthesized.

EXAMPLE 5

In a similar manner to Example 2 except that 1-(4-dimethylaminonaphthyl)-3-(2,4,5-trimethoxyphenyl)-2-propynyl-1-one obtained in Referential Example 10(c) and 1,1-dimethylguanidine sulfate were used as raw materials, Compound 5 shown in Table 2 was synthesized.

EXAMPLE 6

In a similar manner to Example 2 except that 1-(3-pyridyl)-3-(2,4,5-trimethoxyphenyl)-2-propynyl-1-one obtained in Referential Example 10(d) and 1,1-dimethylguanidine sulfate were used as raw materials. Compound 6 shown in Table 2 was synthesized.

EXAMPLE 7

In a similar manner to Example 2 except that 1-(4-dimethylaminophenyl)-3-(2,4,5-trimethoxyphenyl)-2-propynyl-1-one obtained in Referential Example 10(b) and 1,1-dimethylguanidine sulfate were used as raw materials. Compound 7 shown in Table 2 was synthesized.

EXAMPLE 8

In a similar manner to Example 2 except that 1-(4-(2-dimethylaminoethyleneoxy)phenyl)-3-(2,4,5-trimethoxyphenyl)-2-propynyl-1-one obtained in Referential Example 10(e) and 1,1-dimethylguanidine sulfate were used as raw materials, Compound 8 shown in Table 2 was synthesized.

EXAMPLE 9

In a similar manner to Example 1 except that 1,3-di(2,4, 5-trimethoxyphenyl)-2-propynyl-1-one obtained in Referential Example 10(a) and 1,1-diethylguanidine sulfate were used as raw materials, Compound 9 shown in Table 3 was synthesized.

EXAMPLE 10

In a similar manner to Example 2 except that 1-(4-piperidylphenyl)-3-(2,4,5-trimethoxyphenyl)-2-propynyl-1-one obtained in Referential Example 10(g) and 1,1-dimethylguanidine sulfate were used as raw materials, Compound 10 shown in Table 3 was synthesized.

EXAMPLE 11

In a similar manner to Example 2 except that 1-(4-chlorophenyl)-3-(2,4,5-trimethoxyphenyl)-2-propynyl-1-one obtained in Referential Example 10(h) and 1,1-dimethylguanidine sulfate were used as raw materials, Compound 11 shown in Table 3 was synthesized.

EXAMPLE 12

In a similar manner to Example 1 except that 1-(2-nitrophenyl)-3-(2,4,5-trimethoxyphenyl)-2-propynyl-1-one obtained in Referential Example 10(i) and 1,1-diethylguanidine sulfate were used as raw materials. Compound 12 shown in Table 3 was synthesized.

EXAMPLE 13

In a similar manner to Example 2 except that 1-(4-(2-imidazolylethyleneoxy)phenyl)-3-(2,4,5-trimethoxyphenyl)-2-propynyl-1-one obtained in Referential Example 17 and 1,1-diethylguanidine sulfate were used as raw materials, Compound 13 shown in Table 4 was synthesized.

EXAMPLE 14

In a similar manner to Example 2 except that 1-(4-methoxyethoxymethoxyphenyl)-3-(2,4,5-trimethoxyphenyl)-2-propynyl-1-one obtained in Referential Example 10(k) and 1,1-diethylguanidine sulfate were used as raw materials, Compound 14 shown in Table 4 was synthesized.

EXAMPLE 15

In a similar manner to Example 2 except that 1-(4-(4-methylpiperazinylethyleneoxy)phenyl)-3-(2,4,5-trimethoxyphenyl)-2-propynyl-1-one and 1,1-diethylguanidine sulfate were used as raw materials, 2-diethylamino-4-(4-(4-methylpiperazinylethylene-oxy)phenyl)-6-(2,4,5-trimethoxyphenyl)pyrimidine was synthesized.

$^1$H-NMR (CDCl$_3$)δ: 1.28(6H,t,J=6.9Hz), 2.30(3H,s), 2.49 (4H,bs), 2.64(4H,bs), 2.85(2H,t,J=5.9Hz), 3.77(4H,q,J=6.9Hz), 3.91(3H,s), 3.92(3H,s), 3.96(3H,s), 4.18(2H,t,J=5.9Hz), 6.61(1H,s), 6.99(2H,d,J=8.9Hz), 7.63(1H,s), 7.81 (1H,s), 8.07(2H,d,J=8.9Hz).

On the product thus obtained, hydrochloric acid was caused to act, whereby Compound 15 shown in Table 4 was synthesized as a hydrochloride.

EXAMPLE 16

In a similar manner to Example 2 except that 1-(4-N-phthaliminoylethyleneoxy)phenyl-3-(2,4,5-trimethoxyphenyl)-2-propynyl-1-one obtained in Referential Example 18 and 1,1-diethylguanidine sulfate were used as raw materials, Compound 16 shown in Table 4 was synthesized.

EXAMPLE 17

In a similar manner to Example 2 except that 1-(2,4-dimethoxyphenyl)-3-(2,4,5-trimethoxyphenyl)-2-propynyl-1-one obtained in Referential Example 10(m) and 1,1-diethylguanidine sulfate were used as raw materials, Compound 17 shown in Table 5 was synthesized.

EXAMPLE 18

In a similar manner to Example 2 except that 1-(2,4-dichlorophenyl)-3-(2,4,5-trimethoxyphenyl)-2-propynyl-1-one obtained in Referential Example 10(n) and 1,1-diethylguanidine sulfate were used as raw materials, Compound 18 shown in Table 5 was synthesized.

EXAMPLE 19

In a similar manner to Example 2 except that 1-(2,5-dimethoxyphenyl)-3-(2,4,5-trimethoxyphenyl)-2-propynyl-1-one obtained in Referential Example 10(o) and 1,1-diethylguanidine sulfate were used as raw materials, Compound 19 shown in Table 5 was synthesized.

EXAMPLE 20

In a similar manner to Example 2 except that 1-(3,4,5-trimethoxyphenyl)-3-(2,4,5-trimethoxyphenyl)-2-propynyl-1-one obtained in Referential Example 10(p) and 1,1-diethylguanidine sulfate were used as raw materials, 2-diethylamino-4-(3,4,5-trimethoxyphenyl)-6-(2,4,5-trimethoxyphenyl)pyrimidine was synthesized.

Melting point: 110°–112° C. $^1$H-NMR (CDCl$_3$)δ: 1.29 (6H,t,J=7.0Hz), 3.77(4H,q,J=7.0Hz), 3.90(3H,s), 3.91(3H,s), 3.92(3H,s), 3.95(9H,s), 6.61(1H,s), 7.37(2H,s), 7.61(1H,s), 7.80(1H,s).

In a 300 ml solution of 30 g of the compound so obtained in ethanol, 11 ml of concentrated hydrochloric acid were added, followed by dissolution under heating. After the reaction mixture was allowed to cool down, the salt precipitated was collected by filtration, whereby 29 g of Compound 20 shown in Table 5 were obtained (yield: 89%).

IR(KBr)cm$^{-1}$: 1127 1215 1245 1264 1279 1324 1336 1399 1423 1453 1467 1509 1521 1561 1587 1606 1625 2936 2948 2968

EXAMPLE 21

In 50 ml of methanol, 1.2 g of aminoiminomethanesulfonic acid were suspended. To the resulting suspension, 0.85 g of piperidine was added under ice cooling, followed by stirring at room temperature for 10 minutes. After the completion of the reaction, the solvent was distilled off, whereby 1,1-(N-piperidyl)guanidine was obtained. In a similar manner to Example 2 except that 1,1-(N-piperidyl)guanidine so obtained and 1,3-di(2,4,5-trimethoxyphenyl)-2-propynyl-1-one obtained in Referential Example 10(a) were used as raw materials, Compound 21 shown in Table 6 was synthesized.

EXAMPLE 22

In 50 ml of methanol, 1.2 g of aminoiminomethanesulfonic acid were suspended. To the resulting suspension, 0.87 g of morpholine was added under ice cooling, followed by stirring at room temperature for 24 hours. After the completion of the reaction, the solvent was distilled off, whereby 1,1-(N-morpholino)guanidine was obtained. To the compound so obtained, 50 ml of a saturated picric acid solution were added to precipitate its salt. The salt so precipitated was collected by filtration, whereby 1.963 g of 1,1-(N-morpholino)guanidine picrate were obtained (yield: 56.7%). In a similar manner to Example 2 except that 1,1-(N-morpholino)guanidine picrate so obtained and 1,3-di(2,4,5-trimethoxyphenyl)-2-propynyl-1-one obtained in Referential Example 10(a) were used as raw materials, Compound 22 shown in Table 6 was synthesized.

IR(KBr)cm$^{-1}$: 586 758 813 859 870 949 1000 1032 1083 1110 1121 1151 1207 1219 1264 1271 1307 1330 1350 1423 1438 1444 1466 1515 1538 1554 1586 1609 2837 2936

EXAMPLE 23

In 50 ml of methanol, 1.2 g of aminoiminomethanesulfonic acid were suspended. To the resulting suspension, 1.0 g of N-methylpiperidine was added under ice cooling, followed by stirring at room temperature for 24 hours. After the completion of the reaction, the solvent was distilled off, whereby 1,1-(N-(N-methyl)piperazinyl)-guanidine was obtained. In a similar manner to Example 2 except that 1,1-(N-(N-methyl)piperazinyl)guanidine so obtained and 1,3-di(2,4,5-trimethoxyphenyl)-2-propynyl-1-one obtained in Referential Example 10(a) were used as raw materials, Compound 23 shown in Table 6 was synthesized.

EXAMPLE 24

In a similar manner to Example 1 except that 1-(3,5-dimethoxy-4-methoxyethoxymethoxyphenyl)-3-(2,4,5-trimethoxyphenyl)-2-propynyl-1-one obtained in Referential Example 10(f) and 1,1-dimethylguanidine sulfate were used as raw materials, 2-dimethylamino-4-(3,5-dimethoxy-4-methoxyethoxymethoxyphenyl)-6-(2,4,5-trimethoxyphenyl)pyrimidine was synthesized. To a 50 ml solution of 10 g of this compound in methanol, a 11 ml solution of 4N hydrochloric acid in ethyl acetate was added under ice cooling, followed by stirring under heat at 50° C. for 4 hours. After the reaction mixture was allowed to cool down, ether was added to precipitate the salt. The salt so precipitated was collected by filtration, whereby 7.12 g of Compound 24 shown in Table 6 were obtained (yield: 79%).

EXAMPLE 25

By using 1-(4-methoxyethoxymethoxyphenyl)-3-(2,4,5-triemethoxyphenyl)-2-propynyl-1-one obtained in Referential Example 10(k) and 1,1-diethylguanidine sulfate as raw materials, 2-diethylamino-4-(4-methoxyethoxymethoxyphenyl)-6-(2,4,5-trimethoxyphenyl)pyrimidine was obtained. In a similar manner to Example 24 except that the compound so obtained was used, Compound 25 shown in Table 7 was synthesized.

EXAMPLE 26

In a similar manner to Example 24 except that 1-(4-methoxyethoxymethoxyphenyl)-3-(2,4,5-trimethoxyphenyl)-2-propynyl-1-one obtained in Referential Example 10(k) and 1,1-dimethylguanidine sulfate were used as raw materials, Compound 26 shown in Table 7 was synthesized.

EXAMPLE 27

To 3 ml of water, 5.4 g of 1-(2'-methanesulfoamide-4',5'-dimethoxyphenyl)-3-(2,4,5-trimethoxyphenyl)-2-propenyl-1-one, 1.3 g of potassium tert-butoxide, 1.75 g of 1,1-diethylguanidine sulfate and 50 ml of dimethylformamide were added successively, followed by stirring under heat at 140° C. for 24 hours. After the reaction mixture was allowed to cool down, the solvent was distilled off under reduced pressure. To the residue, water was added, followed by extraction with ethyl acetate. The extract was then washed with saturated saline and then dried over anhydrous magnesium sulfate. The organic layer was concentrated under reduced pressure and the residue was separated and purified by chromatography on a silica gel column (developing solvent, ethyl acetate: n-hexane), whereby 1.3 g of Compound 27 shown in Table 7 were obtained (yield: 20%).

EXAMPLE 28

In a similar manner to Example 27 except that 1-(4-methylthiophenyl)-3-(2,4,5-trimethoxyphenyl)-2-propenyl-1-one obtained in Referential Example 12(q) and guanidine carbonate were used as raw materials, Compound 28 shown in Table 7 was synthesized.

EXAMPLE 29

In a similar manner to Example 27 except that 1-(4-methylthiophenyl)-3-(2,4,5-trimethoxyphenyl)-2-propenyl-1-one obtained in Referential Example 12(q) and 1,1-dimethylguanidine sulfate were used as raw materials, Compound 29 shown in Table 8 was synthesized.

EXAMPLE 30

In a similar manner to Example 27 except that 1-(4-thiazolyl)-3-(2,4,5-trimethoxyphenyl)-2-propenyl-1-one obtained in Referential Example 12(r) and 1,1-dimethylguanidine sulfate were used as raw materials, Compound 30 shown in Table 8 was synthesized.

IR(KBr)cm$^{-1}$: 593 749 767 812 846 859 1029 1040 1070 1083 1160 1184 1211 1227 1247 1277 1313 1346 1401 1436 1465 1513 1552 1563 1612 2832 2911 2939 3101

EXAMPLE 31

The compound (1.0 g) obtained in Example 3, 10 g of methanesulfonic anhydride and 0.33 ml of dimethylaniline were mixed and they were stirred under heat at 120° C. for 24 hours. The reaction mixture was added as was to methanol. The crystals so precipitated were collected by filtration and dried, whereby 0.97 g of Compound 31 shown in Table 8 was obtained (yield: 69%).

EXAMPLE 32

In 50 ml of acetic anhydride, 3.0 g of the compound obtained in Example 3 were dissolved, followed by stirring under heat at 100° C. for 24 hours. The reaction mixture was left to stand under ice cooling, whereby crystals were precipitated. The crystals so precipitated were collected by filtration and dried, whereby 1.1 g of Compound 32 shown in Table 8 were obtained (yield: 33%).

EXAMPLE 33

In 50 ml of acetic anhydride, 3.0 g of the compound obtained in Example 3 were dissolved, followed by stirring under heat at 100° C. for 24 hours. The reaction mixture was left to stand under ice cooling to cause precipitation. The precipitate so formed was collected by filtration. Ether was added to the filtrate. The crystals so precipitated were collected by filtration and then dried, whereby 1.8 g of Compound 33 shown in Table 9 were obtained (yield: 50%).

EXAMPLE 34

To a mixed solution of 30 ml of acetic acid and 10 ml of ethanol to which 0.85 g of the compound obtained in Example 3 and 1 ml of n-butylaldehyde had been added, 0.13 g of sodium cyanoborohydride was added under ice cooling. The resulting mixture was stirred at room temperature for 72 hours. After the completion of the reaction, the solvent was distilled off under reduced pressure. To the residue, an aqueous solution of sodium hydroxide was added, followed by extraction with ethyl acetate. The organic layer was concentrated under reduced pressure. The residue was separated and purified by chromatography on a silica gel column (developing solvent, ethyl acetate: n-hexane), whereby 0.3 g of Compound 34 shown in Table 9 was obtained (yield: 31%).

EXAMPLE 35

To a mixed solution of 30 ml of acetic acid and 10 ml of ethanol to which 0.85 g of the compound obtained in Example 3 and 1 ml of n-butylaldehyde had been added, 0.13 g of sodium cyanoborohydride was added under ice cooling. The resulting mixture was stirred at room temperature for 8 hours, followed by further addition of 0.13 g of sodium cyanoborohydride. The resulting mixture was stirred at room temperature for 12 hours. After the completion of the reaction, the solvent was distilled off under reduced pressure. To the residue, an aqueous solution of sodium hydroxide was added, followed by extraction with ethyl acetate. The organic layer was concentrated under reduced pressure. The residue was separated and purified by chromatography on a silica gel column (developing solvent, ethyl acetate: n-hexane), whereby 0.37 g of Compound 35 shown in Table 9 was obtained (yield: 34%).

EXAMPLE 36

To 100 ml of ethanol, 15.9 g of the compound obtained in Example 16 and 2 ml of hydrazine 1 hydrate were added, followed by heating under reflux for 4 hours. After the reaction mixture was allowed to cool down, the by-product so precipitated was collected by filtration. The filtrate was concentrated under reduced pressure to precipitate crystals, whereby 11.2 g of Compound 36 shown in Table 9 were obtained (yield: 90%).

EXAMPLE 37

To 100 ml of benzene, 2.47 g of the compound obtained in Example 36, 50 mg of paratoluenesulfonic acid and 0.6 ml of butylaldehyde were added. The resulting mixture was heated under reflux for 24 hours while water was removed using the Dean & Stark apparatus. The solvent was then concentrated under reduced pressure. To the residue, 50 ml of ethanol were added, followed by the addition of 0.21 g of sodium borohydride under ice cooling. The resulting mixture was stirred at room temperature for 12 hours. After the reaction, water was added to the reaction mixture, followed by extraction with chloroform. The extract was washed with saturated saline and then dried over anhydrous magnesium sulfate. The organic layer was concentrated under reduced pressure. The residue was then separated and purified by chromatography on a silica gel column (developing solvent, chloroform: methanol), whereby 2-diethylamino-4-(4-(2-propylaminoethoxy)phenyl)-6-(2,4,5-trimethoxyphenyl) pyrimidine was synthesized.

$^1$H-NMR (CDCl$_3$)δ: 0.93(3H,t,J=7.0Hz), 1.22–1.69(7H, m), 2.69(2H,t,J=7.1Hz), 3.03(2H,t,J=5.2Hz), 3.77(4H,q,J=7.0Hz), 3.90(3H,s), 3.92(3H,s), 3.95(3H,s), 4.14(2H,t,J=5.2Hz), 6.61(1H,s), 6.99(2H,d,J=8.8Hz), 7.63(1H,s), 7.81(1H,s), 8.08(2H,d,J=8.8Hz).

Hydrochloric acid was caused to act on the product, whereby 1.1 g of Compound 37 shown in Table 10 were obtained as a hydrochloride (yield: 40%).

EXAMPLE 38

Under ice cooling, 5 g of the compound obtained in Example 25 were added to a 50 ml dimethylformamide solution to which 0.6 g of 60% sodium hydride had been added, followed by stirring at room temperature for 10 minutes. To the resulting mixture, a solution of dimethylaminoethylene chloride in ethyl ether (said solution being obtained by adding 3.5 g of dimethylaminoethylene chloride hydrochloride and 1 g of sodium hydroxide to 20 ml of ether and 20 ml of water and then fractionating the organic layer) was added, followed by stirring under heat at 100° C. for one hour. After the reaction mixture was allowed to cool down, water was added to precipitate crystals. The crystals so obtained were collected by filtration and then dried, whereby 2-diethylamino-4-(4-(2-dimethylaminoethoxy)phenyl)-6-(2,4,5-trimethoxyphenyl)pyrimidine was synthesized.

$^1$H-NMR (CDCl$_3$)δ: 1.28(6H,t,J=6.9Hz), 2.35(6H,s), 2.76 (2H,t,J=5.8Hz), 3.77(4H,q,J=6.9Hz), 3.91(3H,s), 3.92(3H, s), 3.96(3H,s), 4.13(2H,t,J=5.8Hz), 6.61(1H,s), 7.01(2H,d, J=8.8Hz), 7.63(1H,s), 7.81(1H,s), 8.07(2H,d,J=8.8Hz).

Hydrochloric acid was caused to act on the product, whereby 5.0 g of Compound 38 shown in Table 10 were obtained as a hydrochloride (yield: 85%).

IR(KBr)cm$^{-1}$: 1020 1121 1184 1216 1250 1280 1288 1311 1323 1338 1347 1398 1428 1436 1453 1469 1494 1514 1581 1601 1627 2701 2934 2949 2956 2972 3180 3377 3388 3392 3398 3405 3412 3433 3439 3489

EXAMPLE 39

In a similar manner to Example 38 except that 2-morpholinoethylene chloride hydrochloride was used instead of dimethylaminoethylene chloride hydrochloride as the raw material, 2-diethylamino-4-(4-(2-morpholinoethoxy)phenyl)-6-(2,4,5-trimethoxyphenyl) pyrimidine was synthesized.

$^1$H-NMR (CDCl$_3$)δ: 1.28(6H,t,J=8.9Hz), 2.60(4H,t,J=4.6Hz), 2.84(2H,t,J=5.8Hz), 3.71–3.84(8H,m), 3.91(3H,s), 3.92(3H,s), 3.96(3H,s), 4.19(2H,t,J=5.8Hz), 6.61(1H,s), 6.99(2H,d,J=8.9Hz), 7.63(1H,s), 7.81(1H,s), 8.07(2H,d,J=8.9Hz)

Hydrochloric acid was caused to act on the product, whereby Compound 39 shown in Table 10 was synthesized as a hydrochloride.

EXAMPLE 40

In a similar manner to Example 38 except that 3-dimethylaminopropyl chloride hydrochloride was used instead of dimethylaminoethylene chloride hydrochloride as the raw material, 2-diethylamino-4-(4-(3-dimethylaminopropoxy)phenyl)-6-(2,4,5-trimethoxyphenyl)pyrimidine was synthesized.

$^1$H-NMR (CDCl$_3$)δ: 1.26(6H,t,J=6.9Hz), 1.98(2H,tt,J=7.3,6.5Hz), 2.26(6H,s), 2.47(2H,t,J=7.3Hz), 3.77(4H,q,J=6.9Hz), 3.90(3H,s), 3.92(3H,s), 3.96(3H,s), 4.08(2H,t,J=6.5Hz), 6.61(1H,s), 6.98(2H,d,J=8.4Hz), 7.63(1H,s), 7.81 (1H,s), 8.07(2H,d,J=8.4Hz).

Hydrochloric acid was caused to act on the product, whereby Compound 40 shown in Table 11 was synthesized as a hydrochloride.

EXAMPLE 41

In a similar manner to Example 38 except that 2-(N-piperazinyl)ethylene chloride hydrochloride was used instead of dimethylaminoethylene chloride hydrochloride as the raw material, Compound 41 shown in Table 11 was synthesized.

IR(KBr)cm$^{-1}$: 834 1027 1044 1179 1208 1228 1250 1278 1290 1307 1314 1353 1434 1509 1544 1556 1585 1608 2330 2341 2360 2364 2933

EXAMPLE 42

To a 50 ml solution of dimethylformamide to which 0.6 g of 60% sodium hydride had been added, 5 g of the compound obtained in Example 25 were added under ice cooling, followed by stirring at room temperature for 10 minutes. To the reaction mixture, 2.0 g of t-butyldiphenylsilanoxyethylene iodide were added, followed by stirring at room temperature for 24 hours. Water was added to the reaction mixture and the resulting mixture was extracted with chloroform-ethyl acetate. The extract was washed successively with a 2N aqueous solution of sodium hydroxide and saturated saline and then dried over anhydrous magnesium sulfate. The organic layer was concentrated under reduced pressure. To the concentrate, 100 ml of tetrahydrofuran and 10 ml of 1N-tetrabutylammonium fluoride were added, followed by stirring at room temperature for 2 hours. After the reaction, water was added to the reaction mixture and the resulting mixture was extracted with chloroform. The extract was washed with saturated saline and dried over anhydrous magnesium sulfate. The organic layer was concentrated under reduced pressure. To the residue, methanol was added to precipitate crystals. The crystals so precipitated were collected by filtration and then dried, whereby 0.72 g of Compound 42 shown in Table 11 was obtained (yield: 33%).

EXAMPLE 43

In 40 ml of pyridine, 2.38 g of the compound obtained in Example 25 were dissolved under ice cooling, followed by the dropwise addition of 0.7 ml of phosphorus oxychloride. The resulting mixture was stirred for 40 minutes. The reaction mixture, together with ice, was then poured into a saturated aqueous solution of sodium bicarbonate, followed by the adjustment to pH 1 with concentrated hydrochloric acid. The crystals so precipitated were collected by filtration, washed with water and then dried, whereby 2.5 g of Compound 43 shown in Table 12 were obtained (yield: 90%).

EXAMPLE 44

In 100 ml of methylene chloride, 9.24 g of the compound obtained in Example 38 were dissolved, followed by the dropwise addition of a 50 ml solution of 4.5 g of methachloroperbenzoic acid in methylene chloride. The resulting mixture was reacted at room temperature for 10 minutes. The reaction mixture was concentrated under reduce pressure. The residue was separated and purified by chromatography on a silica gel column (developing solvent, chloroform: methanol). The purified product was then dissolved in 150 ml of ethyl acetate, followed by the addition of a 5.5 ml solution of 4N hydrochloric acid in ethyl acetate. The salt so precipitated was collected by filtration and dried, whereby 8.28 g of Compound 44 shown in Table 12 were obtained (yield: 81%).

EXAMPLE 45 (alternative method for Compound 9)

Compound 9 which has been synthesized in Example 9 and shown in Table 1 can be synthesized by the alternative method as follows:

To 5 ml of isopropanol, 0.1 g of 60% sodium hydride was added, followed by heating to 82° C. To the resulting mixture, 0.36 g of 1,1-diethylguanidine sulfate was added at 50° C., followed by stirring at 82° C. for one hour. After the reaction mixture was cooled to 70° C., 0.4 g of 1,3-di(2,4,5-trimethoxyphenyl)-1,3-propadione obtained in Referential Example 15 was added, followed by stirring at 82° C. for 3 hours and 100° C. for 16 hours. After the completion of the reaction, water was added to the reaction mixture under ice cooling. The solid so precipitated was collected by filtration and then washed with water and diethyl ether, whereby 0.32 g of Compound 9 shown in Table 3 was obtained (yield: 66%).

EXAMPLE 46

In a similar manner to Example 45 except that 1-(2,4,5-trimethoxyphenyl)-3-(3,4,5-trimethoxyphenyl)-1,3-propanedione was used as the raw material instead of 1,3-di(2,4,5-trimethoxyphenyl)-1,3-propanedione, 4-(3,4,5-trimethoxyphenyl)-6-(2,4,5-trimethoxyphenyl)-2-diethylaminopyrimidine was synthesized. Hydrochloric acid was caused to act on the product so obtained, whereby Compound 20 shown in Table 5 was obtained as a hydrochloride.

The data of the invention compounds obtained in the above examples are shown in Tables 1–12.

TABLE 1

| No. | Structural formula | NMR Data 1 |
| --- | --- | --- |
| 1 | (structure with N(CH$_3$)$_2$, three CH$_3$O groups on phenyl, linked to phenyl-CO$_2$CH$_3$) | Melting point: 171–173° C.<br>Solvent CDCl$_3$<br>3.34(6H, s)<br>3.91(3H, s)<br>3.94(3H, s)<br>3.95(3H, s)<br>3.97(3H, s)<br>6.62(1H, s)<br>7.73(1H, s)<br>7.80(1H, s)<br>8.13(2H, bd)<br>8.18(2H, bd) |
| 2 | (structure with N(CH$_3$)$_2$, three CH$_3$O groups on one phenyl, three OCH$_3$ on other phenyl) | Melting point: 177–179° C.<br>Solvent CDCl$_3$<br>3.38(6H, s)<br>3.88(6H, s)<br>3.93(6H, s)<br>3.95(6H, s)<br>6.61(2H, s)<br>7.76(2H, s)<br>7.91(1H, s) |

TABLE 1-continued

| No. | Structural formula | NMR Data 1 |
|---|---|---|
| 3 | (structure: pyrimidine with NH2, flanked by two 2,4,5-trimethoxyphenyl groups) | Melting point: 229–231° C.<br>Solvent CDCl$_3$<br>3.88(6H, s)<br>3.94(6H, s)<br>3.95(6H, s)<br>5.02(2H, bs)<br>6.61(2H, s)<br>7.58(2H, s)<br>7.94(1H, s) |
| 4 | (structure: pyrimidine with NH2, 2,4,5-trimethoxyphenyl and 4-N(CH3)2-phenyl) | Melting point: 174–176° C.<br>Solvent CDCl$_3$<br>3.04(6H, s)<br>3.88(3H, s)<br>3.94(3H, s)<br>3.95(3H, s)<br>5.02(2H, bs)<br>6.61(1H, s)<br>6.77(2H, d, J=8.9Hz)<br>7.58(1H, s)<br>7.67(1H, s)<br>7.98(2H, d, J=8.9Hz) |

TABLE 2

| No. | Structural formula | NMR Data 1 |
|---|---|---|
| 5 | (structure: pyrimidine with N(CH3)2, 2,4,5-trimethoxyphenyl and 4-N(CH3)2-naphthyl) | Melting point: 163–165° C.<br>Solvent CDCl$_3$<br>2.94(6H, s)<br>3.32(6H, s)<br>3.85(3H, s)<br>3.95(6H, s)<br>6.59(1H, s)<br>7.14(1H, d, J=7.9Hz)<br>7.42–7.54(2H, m)<br>7.50(1H, s)<br>7.69(1H, d, J=7.9Hz)<br>7.83(1H, s)<br>8.26–8.34(1H, m)<br>8.47–8.55(1H, m) |
| 6 | (structure: pyrimidine with N(CH3)2, 2,4,5-trimethoxyphenyl and 3-pyridyl) | Melting point: 149–151° C.<br>Solvent CDCl$_3$<br>3.34(6H, s)<br>3.92(3H, s)<br>3.94(3H, s)<br>3.97(3H, s)<br>6.62(1H, s)<br>7.41(1H, dd, J=7.9, 5.0Hz)<br>7.73(1H, s)<br>7.82(1H, s)<br>8.41(1H, ddd, J=1.8, 1.8, 7.9Hz)<br>8.68(1H, dd, J=1.8, 5.0Hz)<br>9.30(1H, d, J=1.8Hz) |
| 7 | (structure: pyrimidine with N(CH3)2, 2,4,5-trimethoxyphenyl and 4-N(CH3)2-phenyl) | Melting point: 206–208° C.<br>Solvent CDCl$_3$<br>3.03(6H, s) 8.06(2H, d, J=8.9Hz)<br>3.32(6H, s)<br>3.88(3H, s)<br>3.93(3H, s)<br>3.95(3H, s)<br>6.61(1H, s)<br>6.78(2H, d, J=8.9Hz)<br>7.61(1H, s)<br>7.77(1H, s) |

TABLE 2-continued

| No. | Structural formula | NMR Data 1 |
|---|---|---|
| 8 | (structure: 2-N(CH₃)₂ pyrimidine with 2,4,5-trimethoxyphenyl and 4-(2-dimethylaminoethoxy)phenyl substituents) | Melting point: 127–129° C.<br>Solvent CDCl₃<br>2.36(6H, s)<br>2.76(2H, t, J=5.8Hz)<br>3.32(6H, s)<br>3.90(3H, s)<br>3.93(3H, s)<br>3.96(3H, s)<br>4.14(2H, t, J=5.8Hz)<br>6.61(1H, s)<br>7.01(2H, d, J=8.8Hz)<br>7.63(1H, s)<br>7.78(1H, s)<br>8.08(2H, d, J=8.8Hz) |

TABLE 3

| No. | Structural formula | NMR Data 1 |
|---|---|---|
| 9 | (structure: 2-N(C₂H₅)₂ pyrimidine with two 2,4,5-trimethoxyphenyl substituents) | Melting point: 150–152° C.<br>Solvent CDCl₃<br>1.28(6H, t, J=6.9Hz)<br>3.75(4H, q, J=6.9Hz)<br>3.89(6H, s)<br>3.92(6H, s)<br>3.95(6H, s)<br>6.61(2H, s)<br>7.79(2H, s)<br>7.91(1H, s) |
| 10 | (structure: 2-N(CH₃)₂ pyrimidine with 2,4,5-trimethoxyphenyl and 4-piperidinophenyl substituents) | Melting point: 177.5–179° C.:<br>Solvent CDCl₃<br>1.57–1.78(6H, m)<br>3.24–3.38(4H, m)<br>3.32(6H, s)<br>3.89(3H, s)<br>3.93(3H, s)<br>3.95(3H, s)<br>6.61(1H, s)<br>6.98(2H, d, J=8.9Hz)<br>7.61(1H, s)<br>7.77(1H, s)<br>8.04(2H, d, J=8.9Hz) |
| 11 | (structure: 2-N(CH₃)₂ pyrimidine with 2,4,5-trimethoxyphenyl and 4-chlorophenyl substituents) | Melting point: 158–160° C.<br>Solvent CDCl₃<br>3.32(6H, s)<br>3.89(3H, s)<br>3.93(3H, s)<br>3.95(3H, s)<br>6.60(1H, s)<br>7.44(2H, d, J=9.0Hz)<br>7.65(1H, s)<br>7.78(1H, s)<br>8.06(2H, d, J=9.0Hz) |
| 12 | (structure: 2-N(CH₃)₂ pyrimidine with 2,4,5-trimethoxyphenyl and 2-nitrophenyl substituents) | Melting point: 155–157° C.<br>Solvent CDCl₃<br>3.22(6H, s)<br>3.89(3H, s)<br>3.93(3H, s)<br>3.95(3H, s)<br>6.58(1H, s)<br>7.48(1H, s)<br>7.52–7.80(4H, m)<br>7.82(1H, s) |

TABLE 4

| No. | Structural formula | NMR Data 1 |
|---|---|---|
| 13 | 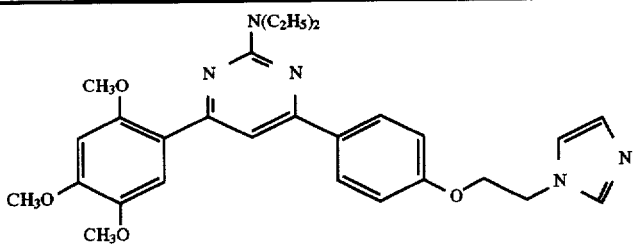 | Melting point: 118–121° C.<br>Solvent CDCl$_3$<br>1.28(6H, t, J=6.9Hz)<br>3.77(4H, q, J=6.9Hz)<br>3.90(3H, s)<br>3.92(3H, s)<br>3.96(3H, s)<br>4.30(2H, t, J=4.9Hz)<br>4.36(2H, t, J=4.9Hz)<br>6.61(1H, s)<br>6.95(2H, d, J=8.9Hz)<br>7.01–7.11(2H, m)<br>7.62(1H, s)<br>7.81(1H, s)<br>8.07(2H, d, J=8.9Hz) |
| 14 | 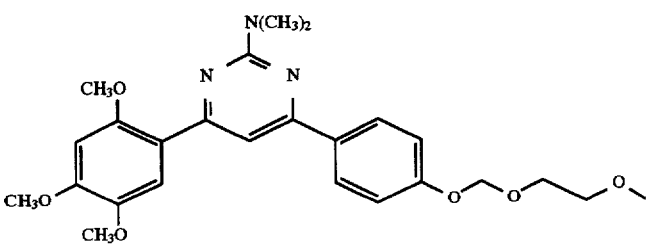 | Melting point: 110–111° C.<br>Solvent CDCl$_3$<br>3.32(6H, s) 6.61(1H, s)<br>3.53(2H, m) 7.14(2H, d, J=8.5Hz)<br>3.58(3H, s) 7.63(1H, s)<br>3.84(2H, m) 7.77(1H, s)<br>3.89(3H, s) 8.06(2H, d, J=8.5Hz)<br>3.93(3H, s)<br>3.95(3H, s)<br>5.33(2H, s) |
| 15 | 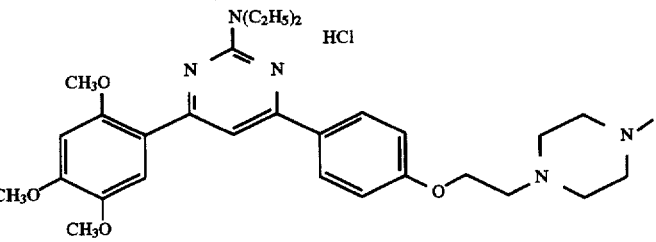 | Melting point: 176–178° C.<br>Solvent DMSO<br>1.23(6H, t, J=6.9Hz)<br>2.84(3H, bs)<br>3.42–4.41(23H, m)<br>4.54(2H, bs)<br>6.84(1H, s)<br>7.18(2H, d, J=8.7Hz)<br>7.63(1H, s)<br>7.65(1H, s)<br>7.18(2H, d, J=8.7Hz)<br>12.07(1H, bs) |
| 16 | 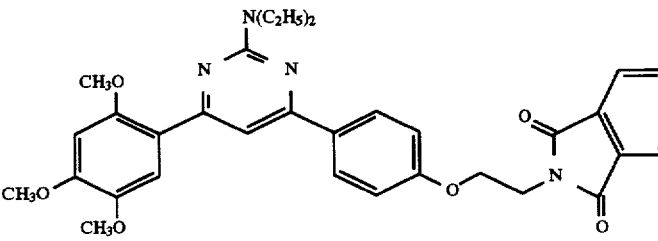 | Melting point: 168–170° C.<br>Solvent CDCl$_3$<br>1.27(6H, t, J=7.0Hz)<br>3.76(4H, q, J=7.0Hz)<br>3.90(3H, s)<br>3.91(3H, s)<br>3.95(3H, s)<br>4.15(2H, t, J=5.7Hz)<br>4.30(2H, t, J=5.7Hz)<br>6.60(1H, s)<br>6.96(2H, d, J=8.9Hz)<br>7.60(1H, s)<br>7.70–7.76(2H, m)<br>7.79(1H, s)<br>7.85–7.92(2H, m)<br>8.04(2H, d, J=8.9Hz) |

TABLE 5

| No. | Structural formula | NMR Data 1 |
|---|---|---|
| 17 | (structure: pyrimidine with N(C₂H₅)₂, 2,4,5-trimethoxyphenyl and 2,4-dimethoxyphenyl groups) | Melting point: 112–113° C.<br>Solvent CDCl₃<br>1.26(6H, t, J=7.0Hz)<br>3.74(4H, q, J=7.0Hz)<br>3.88(6H, s)<br>3.91(3H, s)<br>3.94(3H, s)<br>6.54–6.61(3H, m)<br>7.77(1H, s)<br>7.80(1H, s)<br>8.01(1H, d, J=8.6Hz) |
| 18 | (structure: pyrimidine with N(C₂H₅)₂, 2,4,5-trimethoxyphenyl and 2,4-dichlorophenyl groups) | Melting point: 94–96° C.<br>Solvent CDCl₃<br>1.26(6H, t, J=7.0Hz)<br>3.72(4H, q, J=7.0Hz)<br>3.87(3H, s)<br>3.92(3H, s)<br>3.95(3H, s)<br>6.58(1H, s)<br>7.33(1H, dd, J=2.0, 8.3Hz)<br>7.48(1H, d, J=2.0Hz)<br>7.57(1H, s)<br>7.63(1H, d, J=8.3Hz)<br>7.84(1H, s) |
| 19 | (structure: pyrimidine with N(C₂H₅)₂, 2,4,5-trimethoxyphenyl and 2,3-dimethoxyphenyl groups) | Melting point: 129–131° C.<br>Solvent CDCl₃<br>1.27(6H, t, J=7.0Hz)<br>3.75(4H, q, J=7.0Hz)<br>3.83(3H, s)<br>3.84(3H, s)<br>3.87(3H, s)<br>3.91(3H, s)<br>3.94(3H, s)<br>6.59(1H, s)<br>6.92(2H, d, J=1.0Hz)<br>7.60–7.61(1H, m)<br>7.78(1H, s)<br>7.83(1H, s) |
| 20 | (structure: pyrimidine with N(C₂H₅)₂·HCl, 2,4,5-trimethoxyphenyl and 3,4,5-trimethoxyphenyl groups) | Melting point: 145–148° C.<br>Solvent DMSO<br>1.25(6H, t, J=6.9Hz)<br>3.64–4.06(22H, m)<br>6.85(1H, s)<br>7.43(2H, s)<br>7.62(1H, s)<br>7.69(1H, s) |

TABLE 6

| No. | Structural formula | NMR Data 1 |
|---|---|---|
| 21 | 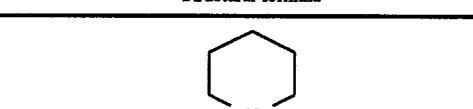 | Melting point: 155–156° C.<br>Solvent CDCl₃<br>1.68(6H, bs)<br>3.88(6H, s)<br>3.92(4H, bs)<br>3.93(6H, s)<br>3.94(6H, s)<br>6.60(2H, s)<br>7.71(2H, s)<br>7.87(1H, s) |

TABLE 6-continued

| No. | Structural formula | NMR Data 1 |
|---|---|---|
| 22 | 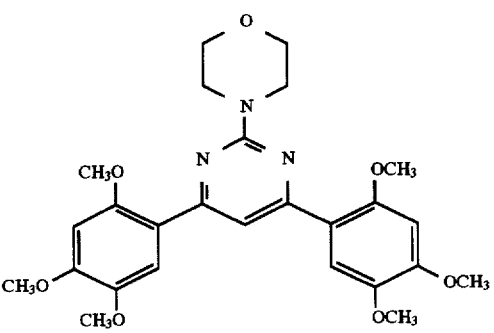 | Melting point: 173–175° C.<br>Solvent CDCl$_3$<br>3.78–3.98(8H, m)<br>3.89(6H, s)<br>3.93(6H, s)<br>3.95(6H, s)<br>6.61(2H, s)<br>7.68(2H, s)<br>7.97(1H, s) |
| 23 | 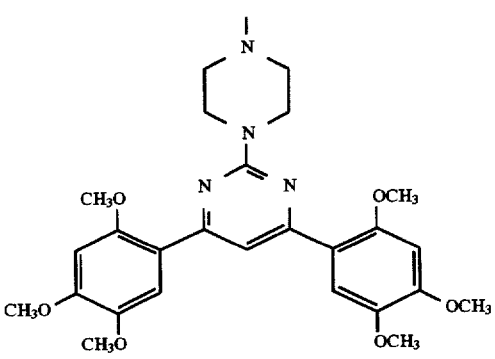 | Melting point: 205–207° C.<br>Solvent CDCl$_3$<br>2.37(3H, s)<br>3.77–4.06(8H, m)<br>3.88(6H, s)<br>3.93(6H, s)<br>3.95(6H, s)<br>6.61(2H, s)<br>7.68(2H, s)<br>7.92(1H, s) |
| 24 | 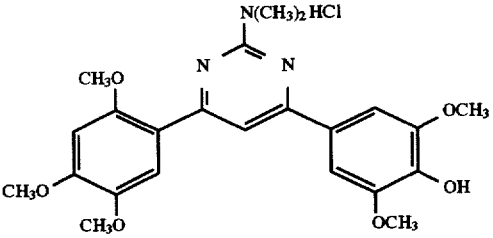 | Melting point: 176–179° C.<br>Solvent DMSO<br>3.31(6H, s)<br>3.80(3H, s)<br>3.88(3H, s)<br>3.91(6H, s)<br>3.93(3H, s)<br>6.87(1H, s)<br>7.50(2H, s)<br>7.57(1H, s)<br>7.72(1H, s)<br>8.32(1H, s) |

TABLE 7

| No. | Structural formula | NMR Data 1 |
|---|---|---|
| 25 | 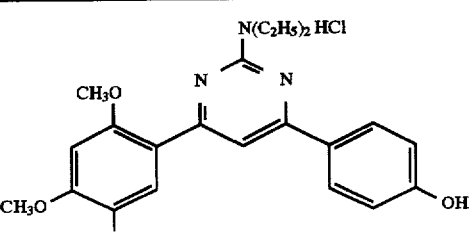 | Melting point: 210–222(dec.) °C.<br>Solvent DMSO<br>1.25(6H, t, J=6.9Hz)<br>3.76(4H, q, J=6.9Hz)<br>3.80(3H, s)<br>3.91(3H, s)<br>3.93(3H, s)<br>6.86(1H, s)<br>6.96(2H, d, J=8.4Hz)<br>7.56(1H, s)<br>7.62(1H, s)<br>8.09(2H, d, J=8.4Hz) |

TABLE 7-continued

| No. | Structural formula | NMR Data 1 |
|---|---|---|
| 26 | (structure: 4-[2-(dimethylamino)pyrimidin-4-yl substituted]; 2,4,5-trimethoxyphenyl and 4-hydroxyphenyl groups) | Melting point: 172–175° C.<br>Solvent CDCl₃<br>3.31(6H, s)<br>3.88(3H, s)<br>3.92(3H, s)<br>3.94(3H, s)<br>5.90(1H, br)<br>6.60(1H, s)<br>6.88(2H, d, J=8.9Hz)<br>7.60(1H, s)<br>7.75(1H, s)<br>8.02(2H, d, J=8.9Hz) |
| 27 | (structure: 2-(dimethylamino)pyrimidine with 2,4,5-trimethoxyphenyl and 2-NHSO₂CH₃-4,5-dimethoxyphenyl groups) | Melting point: 225–227° C.<br>Solvent CDCl₃<br>2.82(3H, s)<br>3.31(6H, s)<br>3.92(3H, s)<br>3.94(3H, s)<br>3.95(3H, s)<br>3.97(6H, s)<br>6.61(1H, s)<br>7.32(1H, s)<br>7.38(1H, s)<br>7.61(1H, s)<br>7.80(1H, s)<br>12.79(1H, bs) |
| 28 | (structure: 2-aminopyrimidine with 2,4,5-trimethoxyphenyl and 4-(methylthio)phenyl groups) | Melting point: 148–150° C.<br>Solvent CDCl₃<br>2.53(3H, s)<br>3.89(3H, s)<br>3.93(3H, s)<br>3.95(3H, s)<br>5.11(2H, s)<br>6.60(1H, s)<br>7.33(2H, d, J=8.0Hz)<br>7.60(1H, s)<br>7.73(1H, s)<br>7.98(2H, d, J=8.0Hz) |

TABLE 8

| No. | Structural formula | NMR Data 1 |
|---|---|---|
| 29 | (structure: 2-(dimethylamino)pyrimidine with 2,4,5-trimethoxyphenyl and 4-(methylthio)phenyl groups) | Melting point: 159–160° C.<br>Solvent CDCl₃<br>2.53(3H, s)<br>3.32(6H, s)<br>3.89(3H, s)<br>3.92(3H, s)<br>3.95(3H, s)<br>6.61(1H, s)<br>7.32(2H, d, J=8.0Hz)<br>7.65(1H, s)<br>7.77(1H, s)<br>8.06(2H, d, J=8.0Hz) |
| 30 | (structure: 2-(dimethylamino)pyrimidine with 2,4,5-trimethoxyphenyl and thiazol-2-yl groups) | Melting point: 144–147° C.<br>Solvent CDCl₃<br>3.30(6H, s)<br>3.92(6H, s)<br>3.95(3H, s)<br>6.59(1H, s)<br>7.44(1H, d, J=3.3Hz)<br>7.78(1H, s)<br>7.95(1H, d, J=3.3Hz)<br>8.03(1H, s) |

TABLE 8-continued

| No. | Structural formula | NMR Data 1 |
|---|---|---|
| 31 | (structure with NHSO₂CH₃ pyrimidine substituent, flanked by 2,4,5-trimethoxyphenyl groups) | Melting point: 238–241° C.<br>Solvent CDCl₃<br>3.47(3H, bs)<br>3.92(6H, s)<br>3.93(6H, s)<br>3.97(6H, s)<br>6.59(2H, s)<br>7.70(2H, s)<br>8.35(1H, s) |
| 32 | (structure with NHCOCH₃ pyrimidine substituent, flanked by 2,4,5-trimethoxyphenyl groups) | Melting point: 203–206° C.<br>Solvent CDCl₃<br>2.69(3H, bs)<br>3.94(12H, s)<br>3.97(6H, s)<br>6.62(2H, s)<br>7.74(2H, s)<br>8.01(1H, bs)<br>8.50(1H, s) |

TABLE 9

| No. | Structural formula | NMR Data 1 |
|---|---|---|
| 33 | (structure with N(COCH₃)₂ pyrimidine substituent, flanked by 2,4,5-trimethoxyphenyl groups) | Melting point: 191–193° C.<br>Solvent CDCl₃<br>2.39(6H, s)<br>3.93(6H, s)<br>3.95(6H, s)<br>3.97(6H, s)<br>6.62(2H, s)<br>7.65(2H, s)<br>8.72(1H, s) |
| 34 | (structure with HN-butyl pyrimidine substituent, flanked by 2,4,5-trimethoxyphenyl groups) | Melting point: 159.5–160.5° C.<br>Solvent CDCl₃<br>0.97(3H, t, J=7.3Hz)<br>1.46(2H, tq, J=7.3, 7.9Hz)<br>1.65(2H, tt, J=6.9, 7.9Hz)<br>3.55(2H, q, J=6.9Hz)<br>3.88(6H, s)<br>3.93(6H, s)<br>3.95(6H, s)<br>5.10(1H, bs)<br>6.60(2H, s)<br>7.66(2H, s)<br>7.89(1H, s) |
| 35 | (structure with N,N-dibutyl pyrimidine substituent, flanked by 2,4,5-trimethoxyphenyl groups) | Melting point: 140–141° C.<br>Solvent CDCl₃<br>0.96(6H, t, J=7.4Hz)<br>1.41(4H, tq, J=7.4, 7.4Hz)<br>1.71(4H, tt, J=7.4, 7.4Hz)<br>3.68(4H, t, J=7.4Hz)<br>3.88(6H, s)<br>3.92(6H, s)<br>3.95(6H, s)<br>6.61(2H, s)<br>7.80(2H, s)<br>7.96(1H, s) |

TABLE 9-continued

| No. | Structural formula | NMR Data 1 |
|---|---|---|
| 36 | 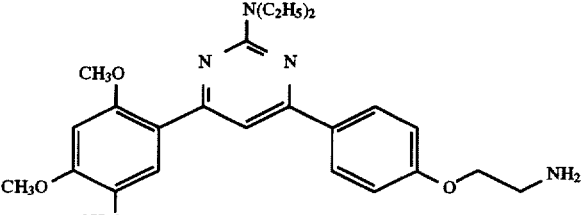 | Melting point: 117–119° C.<br>Solvent CDCl$_3$<br>1.28(3H, t, J=7.0Hz)<br>3.12(2H, t, J=5.1Hz)<br>3.78(2H, q, J=7.0Hz)<br>3.91(3H, s)<br>3.92(3H, s)<br>3.96(3H, s)<br>4.06(2H, t, J=5.1Hz)<br>6.61(1H, s)<br>7.00(2H, d, J=8.9Hz)<br>7.63(1H, s)<br>7.81(1H, s)<br>8.08(2H, d, J=8.9Hz) |

TABLE 10

| No. | Structural formula | NMR Data 1 |
|---|---|---|
| 37 | 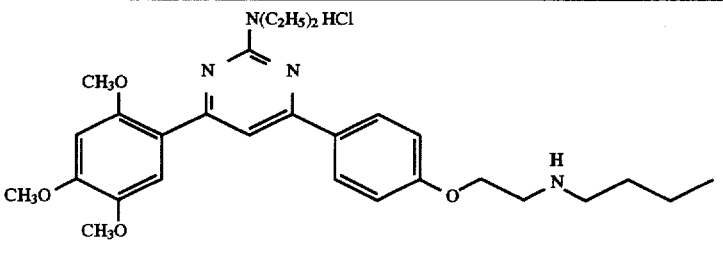 | Melting point: 154–157° C.<br>Solvent DMSO<br>0.91(3H, t, J=7.3Hz)<br>1.24(6H, t, J=6.8Hz)<br>1.29–1.42(2H, m)<br>1.59–1.73(2H, m)<br>2.89–3.04(2H, m)<br>3.10–3.22(2H, m)<br>3.75(4H, q, J=6.8Hz)<br>3.79(3H, s)<br>3.90(3H, s)<br>3.93(3H, s)<br>4.41(2H, bs)<br>6.85(1H, s)<br>7.17(2H, d, J=8.6Hz)<br>7.63 (1H, s)<br>7.67(1H, s)<br>8.17(2H, d, J=8.6Hz)<br>9.27(2H, bs) |
| 38 | 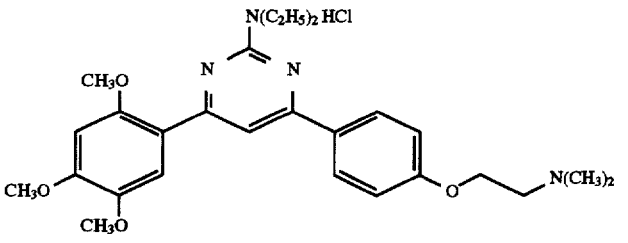 | Melting point: 131–134° C.<br>Solvent DMSO<br>1.25(6H, t, J=6.9Hz)<br>2.84(3H, s)<br>2.86(3H, s)<br>3.49–3.63(2H, m)<br>3.75(4H, q, J=6.9Hz)<br>3.79(3H, s)<br>3.91(3H, s)<br>3.94(3H, s)<br>4.50(2H, t, J=5.0Hz)<br>6.86(1H, s)<br>7.19(2H, d, J=8.8Hz)<br>7.62(1H, s)<br>7.67(1H, s)<br>8.17(2H, d, J=8.8Hz)<br>10.99(1H, bs) |
| 39 | 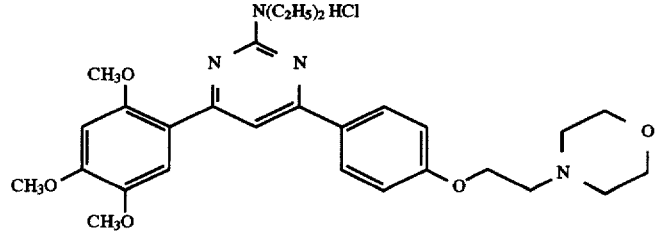 | Melting point: 170–172° C.<br>Solvent DMSO<br>1.23(6H, t, J=7.3Hz)<br>3.41–4.09(23H, m)<br>4.57(2H, bs)<br>6.84(1H, s)<br>7.17(2H, d, J=8.8Hz)<br>7.65(1H, s)<br>7.66(1H, s)<br>8.12(2H, d, J=8.8Hz)<br>11.64(1H, bs) |

TABLE 11

| No. | Structural formula | NMR Data 1 |
|---|---|---|
| 40 | 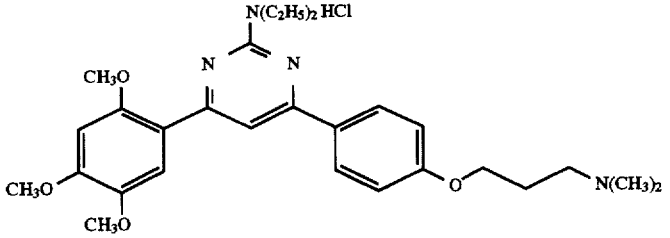 | Melting point: 103–106° C.<br>Solvent DMSO<br>1.25(6H, t, J=6.9Hz)<br>2.13–2.29(2H, m)<br>2.27(3H, s)<br>2.78(6H, s)<br>3.16–3.29(2H, m)<br>3.77(4H, q, J=6.9Hz)<br>3.80(3H, s)<br>3.91(3H, s)<br>3.94(3H, s)<br>4.19(2H, t, J=6.1Hz)<br>6.87(1H, s)<br>7.13(2H, d, J=8.8Hz)<br>7.60(1H, s)<br>7.67(1H, s)<br>8.18(2H, d, J=8.8Hz)<br>11.01(1H, bs) |
| 41 | 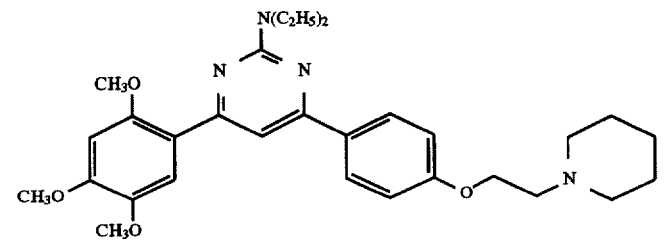 | Melting point: 127–129° C.<br>Solvent CDCl$_3$<br>1.29(6H, t, J=6.9Hz)<br>1.40–1.69(6H, m)<br>2.44–2.59(4H, m)<br>2.80(2H, t, J=6.1Hz)<br>3.77(4H, q, J=6.9Hz)<br>3.90(3H, s)<br>3.92(3H, s)<br>3.95(3H, s)<br>4.17(2H, t, J=6.1Hz)<br>6.61(1H, s)<br>6.99(2H, d, J=8.8Hz)<br>7.63(1H, s)<br>7.81(1H, s)<br>8.07(2H, d, J=8.8Hz) |
| 42 | 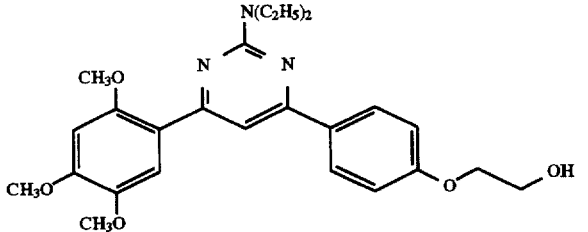 | Melting point: 121–122.5° C.<br>Solvent CDCl$_3$<br>1.28(6H, t, J=7.1Hz)<br>2.05(1H, t, J=7.0Hz)<br>3.78(4H, q, J=7.1Hz)<br>3.91(3H, s)<br>3.92(3H, s)<br>3.96(3H, s)<br>3.99(2H, tt, J=4.6, 7.0Hz)<br>4.16(2H, t, J=4.6Hz)<br>6.61(1H, s)<br>7.01(2H, d, J=8.9Hz)<br>7.63(1H, s)<br>7.81(1H, s)<br>8.09(2H, d, J=8.9Hz) |

TABLE 12

| No. | Structural formula | NMR Data 1 |
|---|---|---|
| 43 | 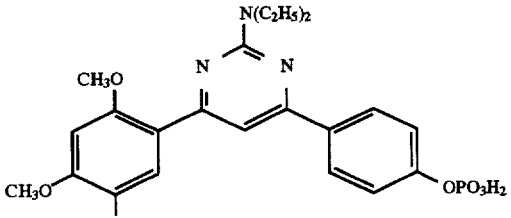 | Metling point: 147–150° C.<br>Solvent DMSO<br>1.23(6H, t, J=7.0Hz)<br>3.73(4H, q, J=7.0Hz)<br>3.77(3H, s)<br>3.89(3H, s)<br>3.93(3H, s)<br>6.83(1H, s)<br>7.33(2H, d, J=8.8Hz)<br>7.66(1H, s)<br>7.68(1H, s)<br>8.10(2H, d, J=8.8Hz) |

TABLE 12-continued

| No. | Structural formula | NMR Data 1 |
|---|---|---|
| 44 | [Structure: trimethoxyphenyl-pyrimidine with N(C₂H₅)₂·HCl and phenyl-O-CH₂CH₂-N(CH₃)₂] | Melting point: 129–132° C.<br>Solvent CDCl₃<br>1.30(6H, t, J=7.0Hz)<br>3.93(6H, s)<br>3.82(4H, q, J=7.0Hz)<br>3.93(3H, s)<br>3.94(3H, s)<br>3.96(3H, s)<br>4.39(2H, bs)<br>4.61(2H, bs)<br>6.61(1H, s)<br>7.01(2H, d, J=8.6Hz)<br>7.61(1H, s)<br>7.75(1H, s)<br>8.09(2H, d, J=8.6Hz)<br>13.41(1H, bs) |

Test 1

To a 96-well microplate, HUVEC (human umbilical vein endothelial cell; product of Kurabo Industries Ltd.) was added in an amount of 3000 cells per well, followed by culturing in 200 μl of RPMI-1640 medium (Nissui Pharmaceutical Co., Ltd.) containing 10 μg/ml of ECGS (Endothelial Cell Growth Supplement; Collaborative Co., Ltd.), 3 ng/ml of EGF (Epithelial Growth Factor; product of Genzyme Co., Ltd.) and 2% fatal calf serum at 37° C. for 48 hours using 5% $CO_2$. To each well, 0.1 μCi (3.7 KBq) of $^3$H-Tymidine was added, followed by culturing for 17 hours. Then, the cells were collected on a glass filter and washed with 5% trichloroacetic acid and ethanol. The radioactivity taken in was measured by a β-plate (Pharmacia Laboratories, Inc.). The concentration showing a 50% growth inhibitory activity ($IC_{50}$) was calculated with a control as 100%. The results are shown in Table 13.

TABLE 13

| Compound No. | $IC_{50}$ (μM) |
|---|---|
| 2 | 0.22 |
| 3 | 0.25 |
| 8 | 1.1 |
| 9 | 0.36 |
| 17 | 0.53 |
| 20 | 0.53 |
| 24 | 0.21 |
| 27 | 0.068 |
| 30 | 0.70 |
| 31 | 0.52 |
| 41 | 1.7 |
| 43 | 0.33 |

Formulation Examples using the invention compounds will be shown below.

Preparation Example 1: Tablets

| Compound 2 | 200 mg |
|---|---|
| Corn starch | 50 mg |
| Microcrystalline cellulose | 50 mg |
| Hydroxypropyl cellulose | 15 mg |
| Lactose | 47 mg |
| Talc | 2 mg |
| Magnesium stearate | 2 mg |
| Ethyl cellulose | 30 mg |
| Unsaturated glyceride | 2 mg |
| Titanium dioxide | 2 mg |

Tablets each 400 mg in weight were prepared according to the above formulation in a manner known per se in the art.

Preparation Example 2: Granules

| Compound 3 | 300 mg |
|---|---|
| Lactose | 540 mg |
| Corn starch | 100 mg |
| Hydroxypropyl cellulose | 50 mg |
| Talc | 10 mg |

Granule packages, each package containing 1000 mg, were prepared according to the above formulation in a manner known per se in the art.

Preparation Example 3: Capsules

| Compound 8 | 200 mg |
|---|---|
| Lactose | 30 mg |
| Corn starch | 50 mg |
| Microcrystalline cellulose | 10 mg |
| Magnesium stearate | 3 mg |

Capsules each 293 mg in weight were prepared according to the above formulation in a manner known per se in the art.

Preparation Example 4: Injections

| Compound 9 | 100 mg |
|---|---|
| Sodium chloride | 3.5 mg |
| Distilled water for injection | q.s. |
| (2 ml per ampoule) | |

Injections were prepared according to the above formulation in a manner known per se in the art.

Preparation Example 5: Syrups

| Compound 20 | 200 mg |
|---|---|
| Refined sugar | 60 g |
| Ethyl parahydroxybenzoate | 5 mg |
| Butyl parahydroxybenzoate | 5 mg |
| Perfume | q.s. |
| Colorant | q.s. |
| Purified water | q.s. |

Syrups were prepared according to the above formulation in a manner known per se in the art.

Preparation Example 6: Suppositories

| | |
|---|---|
| Compound 24 | 300 mg |
| "Witepsol W-35" (trade mark; mono-, di- and triglyceride mixture of a saturated fatty acid from lauric acid to stearic acid; product of Dynamite Novel) | 1400 mg |

Suppositories were prepared according to the above formulation in a manner known per se in the art.

Capability of Exploitation in Industry

A 4,6-diarylpyrimidine derivative according to the present invention has excellent neovascular inhibitory action so that it is useful for the treatment and prevention of diseases caused by the abnormal neovascular formation such as rheumatism, cancer, diabetic retinopathy and psoriasis.

We claim:

1. A 4,6-diarylpyrimidine derivative represented by the following formula (1):

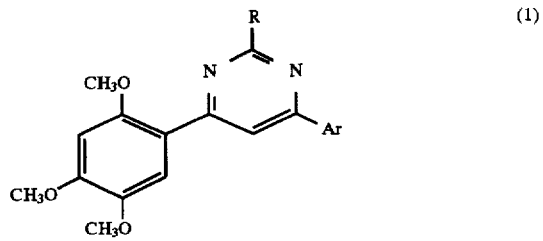

wherein R represents a monocyclic 5- or 6-membered heterocyclic group having from 1–4 nitrogen atoms and 0–1 oxygen or sulfur atoms and which may be substituted by one to four lower alkyl groups or a group —N(R$^1$)R$^2$, said R$^1$ and R$^2$ being the same or different and independently representing a hydrogen atom, a lower alkyl group, a linear or branched C$_{1-6}$ acyl group or a lower alkylsulfonyl group, and Ar represents a phenyl, naphthyl or aromatic, monocyclic 5- or 6-membered heterocyclic group having from 1–4 nitrogen atoms and 0–1 oxygen or sulfur atoms which may have one to four substituents selected from the group consisting of a hydroxy group; lower alkylsulfoimide group; lower alkylthio group; lower alkoxycarbonyl group; amino group which may be substituted by 1–2 lower alkyl groups; halogen atom; nitro group; phosphoric acid residue; monocyclic 5- or 6-membered heterocyclic group having from 1–4 nitrogen atoms and 0–1 oxygen or sulfur atoms which may be substituted by 1–3 lower alkyl groups; and a lower alkoxy group; or a salt thereof.

2. A 4,6-diarylpyrimidine derivative or salt thereof according to claim 1, wherein in the formula (1), the phenyl, naphthyl or aromatic, heterocyclic monocyclic 5- or 6-membered heterocyclic group represented by Ar has one to three substituents selected from the group consisting of a hydroxyl group, a lower alkylsulfoamide group, a lower alkylthio group, a lower alkoxycarbonyl group, an amino group which may be substituted by one or two lower alkyl groups, a halogen atom, a nitro group, a phosphoric acid residue, a 5- or 6-membered heterocyclic group having from 1–4 nitrogen atoms and 0–1 oxygen or sulfur atoms which may be substituted by one to three lower alkyl groups, and a lower alkoxy group which may contain a substituent, the substituent on said lower alkoxy group being a hydroxyl group, a polyether group, an amino group which may be substituted by one or two lower alkyl groups, an amineoxide group which may be substituted by one or two lower alkyl groups or a monocyclic or a fused-ring 5- or 6-membered heterocyclic group having from 1–4 nitrogen atoms and 0–1 oxygen or sulfur atoms which may be substituted by one to three lower alkyl groups.

3. A 4,6-diarylpyrimidine derivative or salt thereof according to claim 1, wherein in the formula (1), the group represented by Ar is a phenyl group, naphthyl group or aromatic, monocyclic 5- or 6-membered heterocyclic group which contains one to four nitrogen atoms and contains 0 to one sulfur atom, which may contain one to three substituents selected from the group consisting of a hydroxy group; lower alkylsulfoimide group; lower alkylthio group; lower alkoxycarbonyl group; amino group which may be substituted by 1–2 lower alkyl groups; halogen atom; nitro group; phosphoric acid residue; monocyclic 5- or 6-membered heterocyclic group having from 1–4 nitrogen atoms and 0–1 oxygen or sulfur atoms which may be substituted by 1–3 lower alkyl groups; and a lower alkoxy group.

4. A 4,6-diarylpyrimidine derivative or salt thereof according to claim 1, wherein in the formula (1), the group represented by Ar is a phenyl, naphthyl, pyridyl or thiazolyl group which may contain one to three substituents selected from the group consisting of a hydroxy group; lower alkylsulfoimide group; lower alkylthio group; lower alkoxycarbonyl group; amino group which may be substituted by 1–2 lower alkyl groups; halogen atom; nitro group; phosphoric acid residue; monocyclic 5- or 6-membered heterocyclic group having from 1–4 nitrogen atoms and 0–1 oxygen or sulfur atoms which may be substituted by 1–3 lower alkyl groups; and a lower alkoxy group.

5. A 4,6-diarylpyrimidine derivative or salt thereof according to claim 1, wherein in the formula (1), the group represented by Ar is a phenyl group containing one to three substituents selected from the groups shown below in (1) to (4):

(1) a lower alkylsulfoamide group,
(2) an amino group which may be substituted by one or two lower alkyl groups,
(3) a monocyclic 5- or 6-membered heterocyclic group having from 1–4 nitrogen atoms and 0–1 oxygen or sulfur atoms, and
(4) a lower alkoxy group which may be substituted by the following (a) or (b):
 (a) an amino group which may be substituted by one or two lower alkyl groups,
 (b) a monocyclic or fused-ring 5- or 6-membered heterocyclic group having from 1–4 nitrogen atoms and 0–1 oxygen or sulfur atoms which may be substituted by one to three lower alkyl groups.

6. A 4,6-diarylpyrimidine derivative or salt thereof according to claim 1, wherein in the formula (1), the group represented by Ar is substituted with a lower alkoxy group or a phenyl group containing one to three lower alkoxyl groups substituted by an amino group which may be substituted by one or two lower alkyl groups.

7. A 4,6-diarylpyrimidine derivative or salt thereof according to any one of claims 1 to 6, wherein in the formula (1), R represents an amino group which may be substituted by one or two lower alkyl groups.

8. A 4,6-diarylpyrimidine derivative or salt thereof according to any one of claims 1 to 6, wherein in the formula (1), R represents an amino, dimethylamino or diethylamino group.

9. A 4,6-diarylpyrimidine derivative or salt thereof according to claim 1, wherein in the formula (1), the group represented by Ar is a phenyl group containing one to three substituents selected from the groups shown below in (1) to (4):

(1) a lower alkylsulfoamide group, (2) an amino group which may be substituted by one or two lower alkyl groups, (3) a monocyclic 5- or 6-membered heterocyclic group having from 1–4 nitrogen atoms and 0–1 oxygen or sulfur atoms, and (4) a lower alkoxy group which may be substituted by the following (a) or (b):

(a) an amino group which may be substituted by one or two lower alkyl groups, (b) a monocyclic or fused-ring 5- or 6-membered heterocyclic group having from 1–4 nitrogen atoms and 0–1 oxygen or sulfur atoms which may be substituted by one to three lower alkyl groups; and the group represented by R is an amino group which may be substituted by one or two lower alkyl groups.

10. A 4,6-diarylpyrimidine derivative or salt thereof according to claim 1, wherein in the formula (1), the group represented by Ar is substituted with a lower alkoxy group or a phenyl group containing one to three lower alkoxyl groups substituted by an amino group which may be substituted by one or two lower alkyl groups; and R represents an amino, dimethylamino or diethylamino group.

11. A pharmaceutical composition comprising a 4,6-diarylpyrimidine derivative or salt thereof according to any one of claims 1 to 10 and a pharmacologically acceptable carrier.

12. A method for treatment of a disease caused by abnormal neovascular formation, which comprises administering an effective amount of a 4,6-diarylpyrimidine derivative or salt thereof according to any one of claims 1 to 10 to a mammary animal, wherein the disease caused by abnormal neovascular formation is rheumatism, diabetic retinopathy or psoriasis.

* * * * *